(12) United States Patent
Barnell et al.

(10) Patent No.: US 11,479,820 B2
(45) Date of Patent: Oct. 25, 2022

(54) DETECTION METHOD USING EUKARYOTIC CELLS

(71) Applicant: GENEOSCOPY, INC., St. Louis, MO (US)

(72) Inventors: Erica Barnell, St. Louis, MO (US); Andrew Barnell, St. Louis, MO (US); Yiming Kang, Clayton, MO (US); Elizabeth Wurtzler, St. Louis, MO (US)

(73) Assignee: GENEOSCOPY, INC., St. Louis, MO (US)

( * ) Notice: Subject to any disclaimer, the term of this patent is extended or adjusted under 35 U.S.C. 154(b) by 521 days.

(21) Appl. No.: 16/345,437

(22) PCT Filed: Oct. 27, 2017

(86) PCT No.: PCT/US2017/058789
§ 371 (c)(1),
(2) Date: Apr. 26, 2019

(87) PCT Pub. No.: WO2018/081580
PCT Pub. Date: May 3, 2018

(65) Prior Publication Data
US 2019/0271046 A1    Sep. 5, 2019

Related U.S. Application Data

(60) Provisional application No. 62/413,708, filed on Oct. 27, 2016, provisional application No. 62/523,511, filed on Jun. 22, 2017, provisional application No. 62/547,046, filed on Aug. 17, 2017.

(51) Int. Cl.
| | |
|---|---|
| *C12N 15/10* | (2006.01) |
| *C12Q 1/68* | (2018.01) |
| *C12Q 1/6886* | (2018.01) |
| *G01N 33/50* | (2006.01) |
| *G01N 33/574* | (2006.01) |

(52) U.S. Cl.
CPC ....... *C12Q 1/6886* (2013.01); *C12N 15/1003* (2013.01); *C12N 15/1013* (2013.01); *C12N 15/1017* (2013.01); *C12Q 1/68* (2013.01); *G01N 33/5044* (2013.01); *G01N 33/57419* (2013.01); *G01N 33/57446* (2013.01); *C12Q 2600/136* (2013.01); *C12Q 2600/156* (2013.01); *C12Q 2600/158* (2013.01); *G01N 2800/065* (2013.01)

(58) Field of Classification Search
CPC ..................................................... C12Q 1/68
See application file for complete search history.

(56) References Cited

U.S. PATENT DOCUMENTS

| | | | |
|---|---|---|---|
| 8,067,190 B2 | 11/2011 | Uhlen et al. | |
| 2007/0172857 A1 | 7/2007 | Daito et al. | |
| 2008/0145932 A1 | 6/2008 | Matsumura et al. | |
| 2010/0112713 A1 | 5/2010 | Chapkin et al. | |
| 2010/0196889 A1 | 8/2010 | Bankaitis-Davis et al. | |
| 2010/0233712 A1 | 9/2010 | Wang et al. | |
| 2011/0060137 A1 | 3/2011 | Tanigami et al. | |
| 2011/0183332 A1* | 7/2011 | Nagaoka ............. C12Q 1/6883 536/25.4 |
| 2012/0064525 A1 | 3/2012 | Asakura et al. | |
| 2012/0064535 A1 | 3/2012 | Tanigami et al. | |
| 2012/0196827 A1 | 8/2012 | Van Criekinge et al. | |
| 2013/0296191 A1 | 11/2013 | Roepman et al. | |
| 2013/0303398 A1 | 11/2013 | Panja | |
| 2014/0221244 A1 | 8/2014 | Chapman et al. | |
| 2020/0040405 A1 | 2/2020 | Barnell et al. | |
| 2021/0214797 A1 | 7/2021 | Barnell et al. | |

FOREIGN PATENT DOCUMENTS

| | | |
|---|---|---|
| JP | 2007175021 | 7/2007 |
| JP | 2012073260 | 1/2013 |
| WO | 2008093530 | 8/2008 |
| WO | 2010010914 | 1/2010 |
| WO | 2010134245 | 11/2010 |
| WO | 2010134246 | 11/2010 |
| WO | 2014160753 | 10/2014 |
| WO | 2015017537 | 2/2015 |
| WO | 2016176446 | 11/2016 |
| WO | 2018081580 | 5/2018 |

OTHER PUBLICATIONS

Yu et al., "Environmental Enteric Dysfunction Includes a Broad Spectrum of Inflammatory Responses and Epithelial Repair Processes", (2016) GMBGH Cellular and Molecular Gastronterol. And Hepatol. 2(2): 158-174 (Year: 2016).*
Tan et al., "DNA, RNA, and Protein Extraction: The Past and The Present", (2009) J Biomed and Biotech 2009: 1-11 (Year: 2009).*
"Cellsaver Tips" (Alpha Laboratories, 2016) (Year: 2016).*
Biomerieux "Nuclisens Easymag" (Year: 2022).*
Tomlinson et al., "Cell separation: Terminology and practical considerations" (2013) J Tissue Eng 4: 1-14 (Year: 2013).*
BioMerieux SA, "NucliSENS Lysis Buffer" (2015) (Year: 2015).*
Written Opinion of the International Searching Authority for PCT/US2016/029777, dated Dec. 8, 2016.
International Search Report for PCT/US2019/035061, dated Sep. 25, 2019.
Virag, P. et al., "Oxaliplatin induces different cellular and molecular chemoresistance patterns in colorectal cancer cell lines of identical origins," 2013, BMC Genomics, 14(480) pp. 1-16.
Zhai, H. et al., "Inhibition of autophagy and tumor growth in colon cancer by miR-502," 2013, Oncogene, 32, pp. 1570-1579.

(Continued)

*Primary Examiner* — Ethan C Whisenant
(74) *Attorney, Agent, or Firm* — Barnes & Thornburg LLP

(57) ABSTRACT

Provided herein are materials and methods for isolation of eukaryotic nucleic acid from a human or non-human animal stool sample. Also provided are methods of analysis of eukaryotic biomarkers present in a human or non-human animal stool sample.

20 Claims, 17 Drawing Sheets

Specification includes a Sequence Listing.

(56) References Cited

OTHER PUBLICATIONS

Llosa, N.J. et al., "Immune checkpoints expression in MSI versus MSS colorectal cancers and their potential therapeutic implications," 2014, Journal of Clinical Oncology, 32(15) pp. suppl, 3620.
Ahmed, F.E. et al., "Diagnostic MicroRNA Markers to Screen for Sporadic Human Colon Cancer in Stool: I. Proof of Principle," 2013, Cancer Genomics & Proteomics, 10, pp. 93-114.
Barresi, V. et al., "Transcriptome analysis of copper homeostasis genes reveals coordinated upregulation of SLC31A1, SCO1, and COX11 in colorectal cancer," 2016, FEBS Open Bio, 6, pp. 794-806.
Maeda, S. et al., "Decreased Immunoglobulin A Concentrations in Feces, Duodenum, and Peripheral Blood Mononuclear Cells of Dogs with Inflammatory Bowel Disease," 2013, Journal Vet Intern. Medicine, 27, pp. 47-55.
Partial Supplementary European Search Report, related to EP Patent Application No. 17863995.1; dated May 28, 2020.
Jinsheng Yu, et al.: "Environmental Enteric Dysfunction Includes a Broad Spectrum of Inflammatory Responses and Epithelial Repair Processes," CMGH Cellular and Molecular Gastroenterology and Hepatology, vol. 2, No. 2, Mar. 2016 (Mar. 2016), pp. 158-174e1.
Anonymous: "NucliSENS Lysis Buffer," Jan. 1, 2015, XP055696006, Retrieved from the Internet: URL:https://pr.vwr.com/assetsvc/asset/en_US/id/18715711/contents.
Jennifer Stauber, et al.: "Droplet digital PCR quantifies host inflammatory transcripts in feces reliably and reproducibly," Cellular Immunology, vol. 303, Apr. 6, 2016, pp. 43-49, US.
Giuliano Bernal: "Use of RNA isolated from feces as a promising tool for the early detection of colorectal cancer," International Journal of Biological Markers, vol. 27, No. 2, 2012, pp. 82-89.
Nechvatal, et al.: "Fecal collection, ambient preservation, and DNA extraction for PCR amplification of bacterial and human markers from human feces," Journal of Microbiological Methods, Elsevier, Amsterdam, NL, vo. 72, No. 2, Nov. 21, 2007, pp. 124-132.
International Search Report and Written Opinion dated Feb. 14, 2018 for corresponding PCT Application No. PCT/US2017/058789.

* cited by examiner

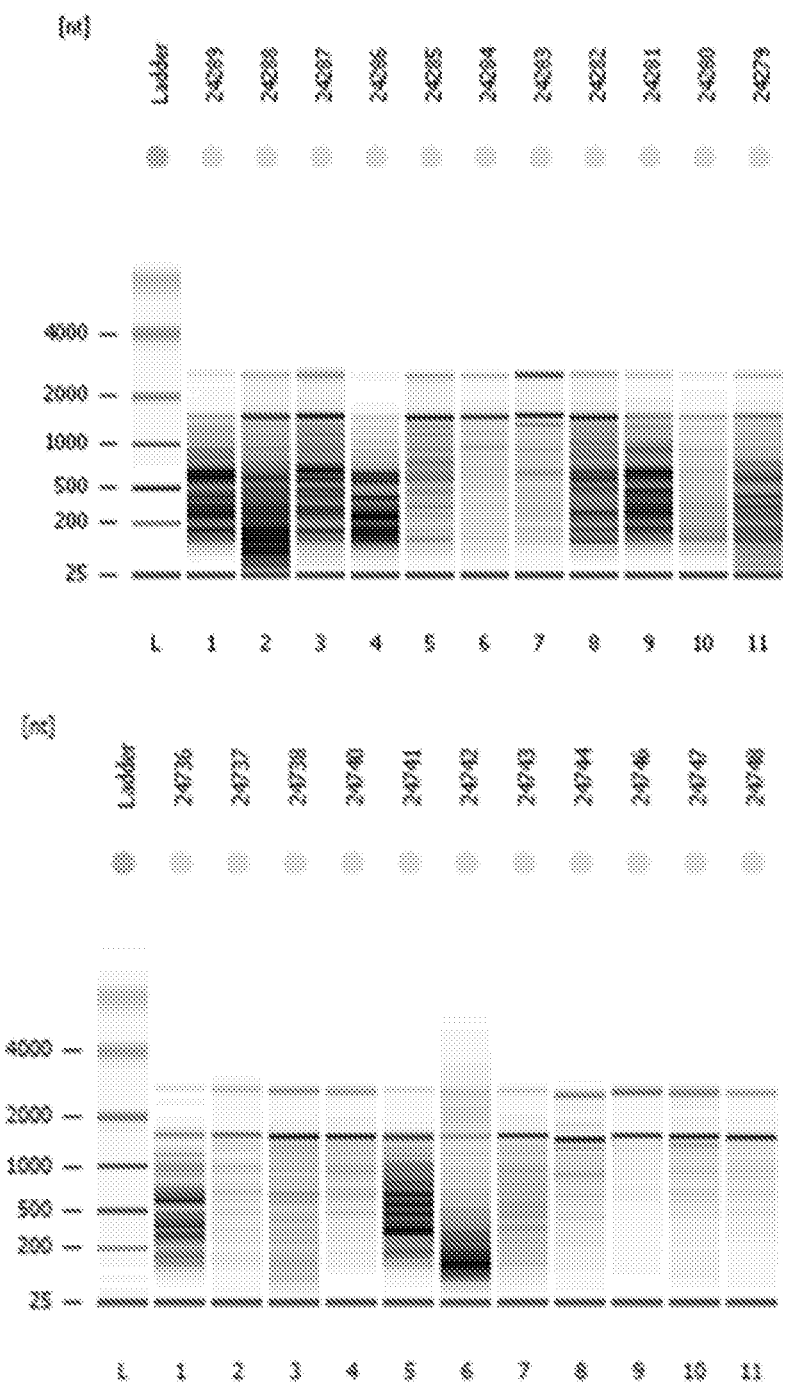
Figure 1: Electrophoresis File Run

Figure 2: Sample Electropherogram
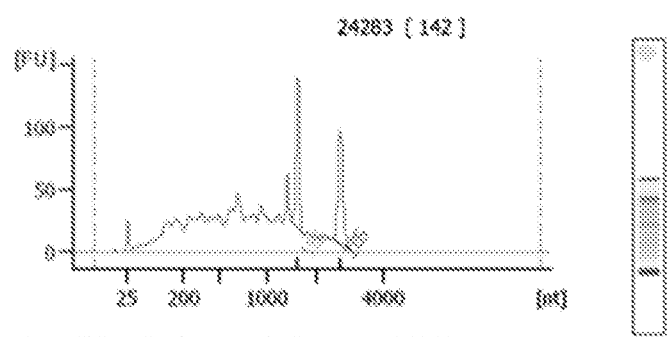

Figure 3: Extraction Summary

| | |
|---|---|
| Number of Samples in Study | 120 |
| Number of Samples Passing QC | 110 |
| Number of Samples Failing QC | 10 |
| Percent of Samples Passing QC | 91.7% |

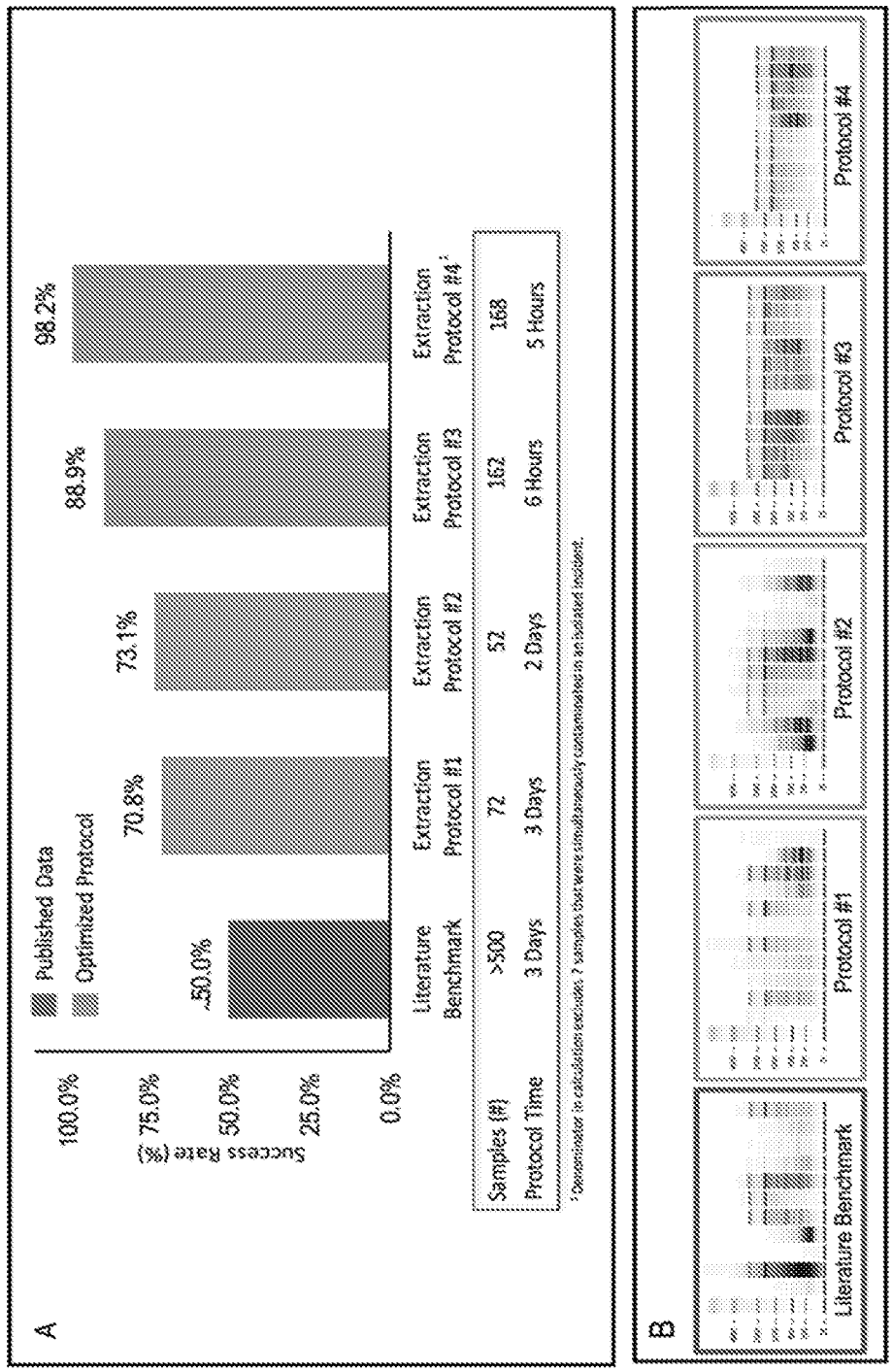
Figure 4: Extraction method to isolate human mRNA biomarkers in stool samples.

Figure 5: Differentially expressed gene annotations.
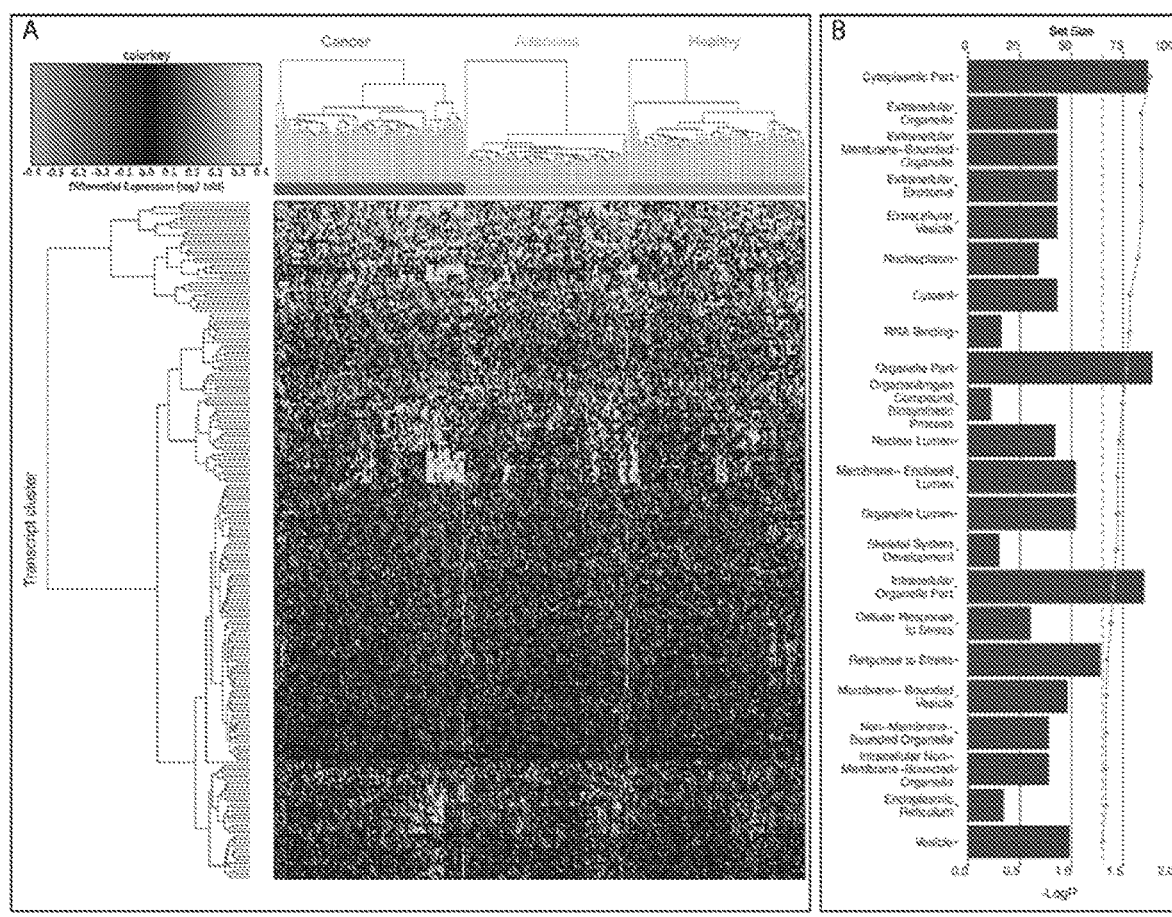

Figure 6: Differentially Expressed Genes. List of gene names based on HUGO nomenclature that are differentially expressed ($p<0.05$) in colorectal neoplasms.

| | | | | |
|---|---|---|---|---|
| COMP | GOLPH3 | FGF6 | CYP1B1 | MAGED4 |
| SACS | KLK4 | TTLL3 | MYB | CHD7 |
| PPP3CB | JAG2 | NCRUPAR | LTA | ID2 |
| ERCC2 | GLRX3 | TFDP1 | CLEC3B | SPARCL1 |
| TAC1 | TNFSF9 | CISH | KISS1R | TUBB3 |
| LRP5 | AIM2 | ASCL1 | FCGR3A | CD151 |
| EPOR | KALRN | PTGER2 | PML | IFNAR1 |
| PARP11 | CCNB1 | POLD1 | TMPRSS4 | FRMPD2 |
| CLDN4 | BVES | SLC25A46 | PLCD1 | OLR1 |
| SCGB2A1 | ERBB3 | CDH22 | MSH5 | GSTA4 |
| IL23A | PTPRS | TLR2 | CDC20 | B4GALT3 |
| GNB2 | MDK | CSRNP3 | RPIA | HMGCR |
| PRKCB | VTCN1 | BRS3 | NCK1 | OTX1 |
| HHEX | ADCY1 | ARID1B | ARL4C | HOXA5 |
| FDPS | PER3 | CITED1 | DHX16 | RPRM |
| GNG8 | THBD | MNX1 | STK11 | RALGDS |
| TMEM158 | IL20RB | PYCR1 | HIST1H2BM | WDR49 |
| ROR1 | TENM1 | CEBPA | PLA2G2A | S100A14 |
| CD276 | TSPEAR | SPINK5 | CDC25C | COL3A1 |
| MIR129-2 | SFRP5 | PEA15 | HK1 | MAPK3 |
| TLR3 | HLA-DQB1 | ZNF135 | NFIB | WNT3A |
| PTGES2 | CSF3R | MYNN | CDHR5 | TCN2 |
| WNT10A | SALL3 | BMP3 | BDNF | BOLL |
| EPHA7 | MUC6 | HLA-DRB1 | CUX1 | MCM5 |
| MAP2K3 | NR4A3 | SHROOM2 | ACY1 | PRMT8 |
| SHC2 | FASN | HK2 | TNS4 | RFX1 |
| NGF | DNAJC14 | CASC2 | ATP1B1 | MDC1 |
| ATP11A | TMEFF2 | CXCL13 | HSPB6 | GDNF |
| SLC12A5 | CSF1R | CCDC129 | TWIST1 | ROBO1 |
| ENO1 | COMT | DPP6 | IGFBP3 | PKMYT1 |
| CD8A | UBD | FNTB | MIR148B | CABLES1 |
| CCNG2 | SALL4 | WNT9A | PTPRU | KDM5C |
| MGST1 | LGR5 | AMD1 | EHMT2 | NID1 |
| ADCY5 | UHRF1 | FDFT1 | EMP1 | SMC1A |
| DHRS9 | MIR223 | PGGT1B | FNTA | CKB |
| FOXL2 | CBLN4 | SPARC | CST1 | PSMB8 |
| GAS5 | NAT10 | SATB1 | THBS2 | ADAMTS9 |
| YY1 | ESRP1 | LMNB2 | ACRBP | C15orf52 |
| HP | MTHFD1 | TDG | FBXL2 | EPHB3 |
| GZMB | PVR | SLC35F5 | FFAR4 | B3GNT8 |

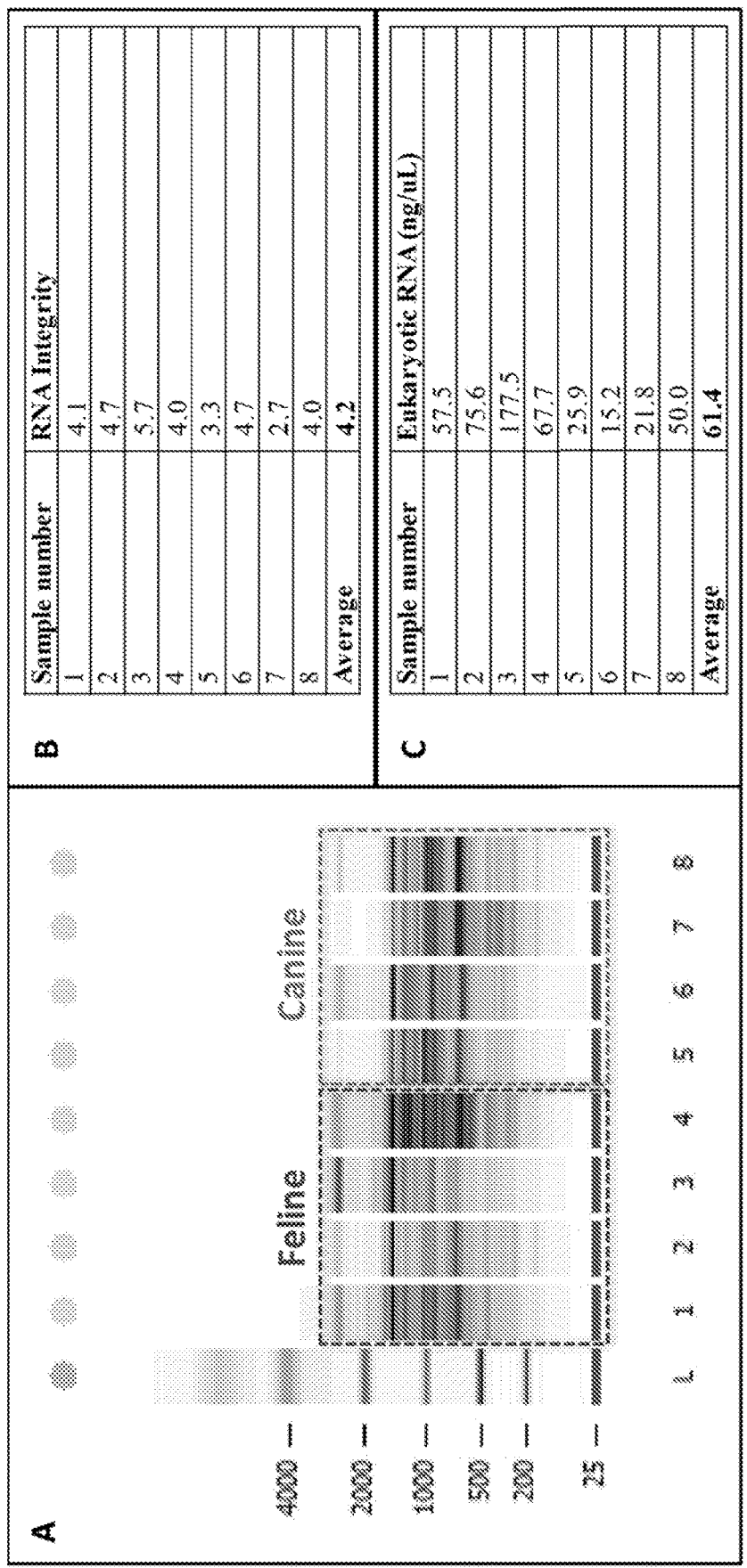
Figure 7: Extraction method to isolate eukaryotic RNA biomarkers in stool samples. A. BioAnalyzer traces for four feline RNA extraction samples and four canine RNA extraction samples. B. RNA Integrity Numbers (RIN) for all eight RNA extraction samples. C. Total estimated eukaryotic RNA concentration for all eight RNA extraction samples.

Figure 8: Canine sample RT-qPCR results. A. RT-qPCR results for positive control C-mu in four canine samples. B. RT-qPCR results for T cell rearrangement specific RNA in four canine samples.
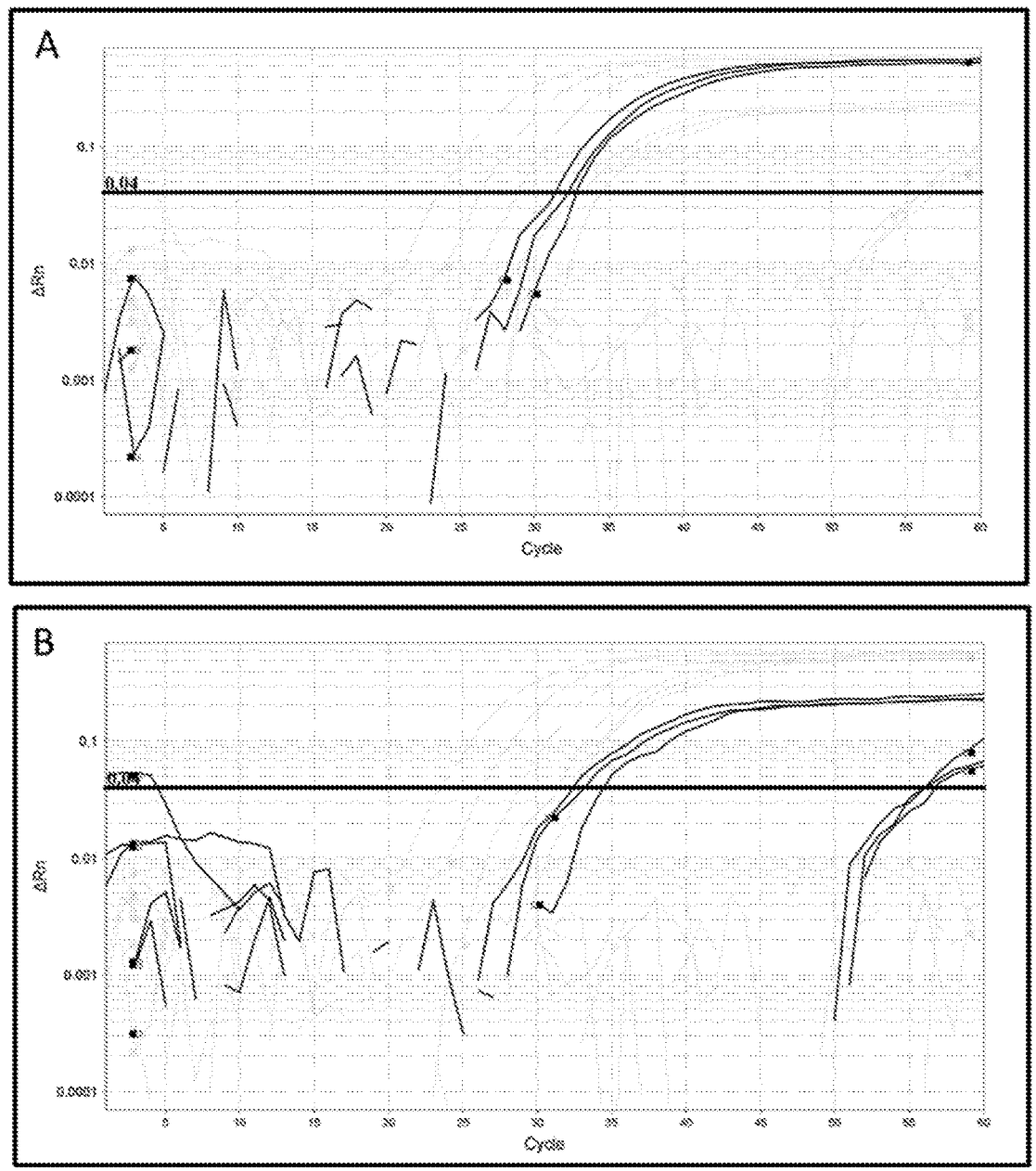

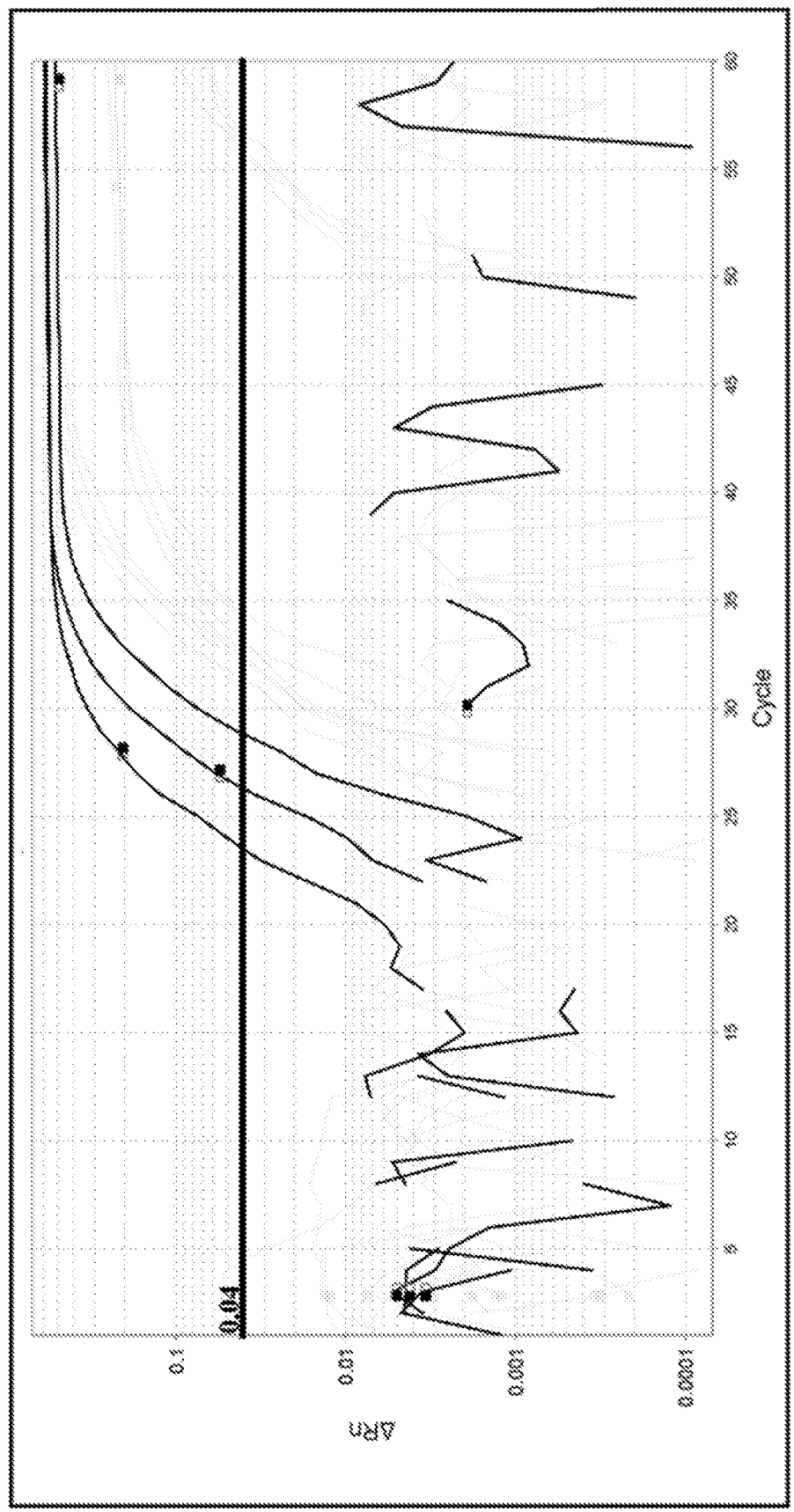
Figure 9: Feline sample RT-qPCR analysis for positive control Actin-B in four feline samples.

Figure 10: Replication analysis for all 70,524 transcript clusters A) Correlations of four technical replicates. B) Correlations of four biological replicates. C) Correlations of technical replicates separate by time.
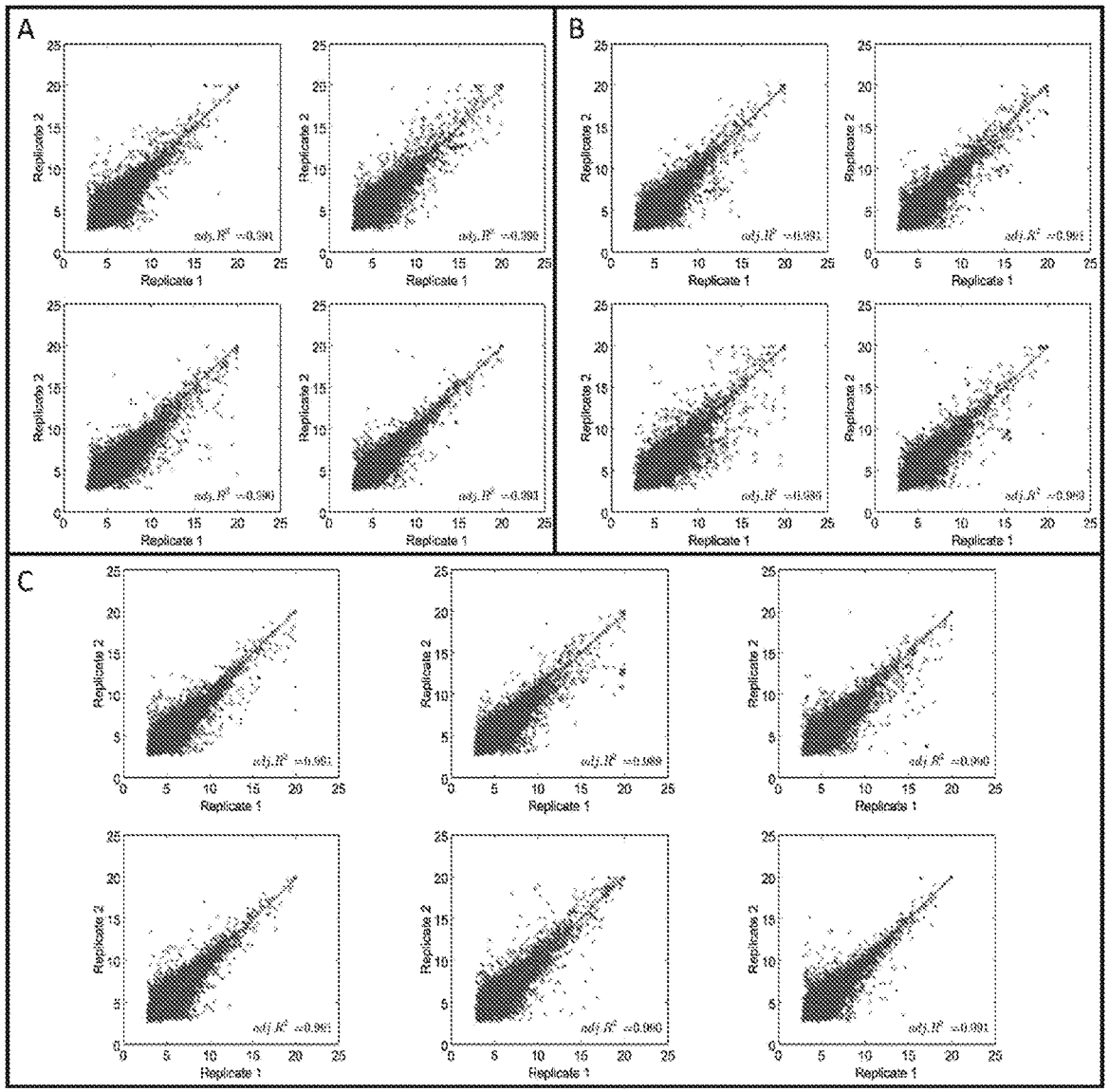

Figure 11: Replication analysis for pre-filtered 5,149 transcript clusters using literature search A) Correlations of four technical replicates. B) Correlations of four biological replicates. C) Correlations of technical replicates separate by time. From top left to bottom right: healthy sample #70, adenoma sample #92, adenoma sample #98, adenoma sample #105, colorectal cancer sample stage II #34, colorectal cancer sample stage IV #36.

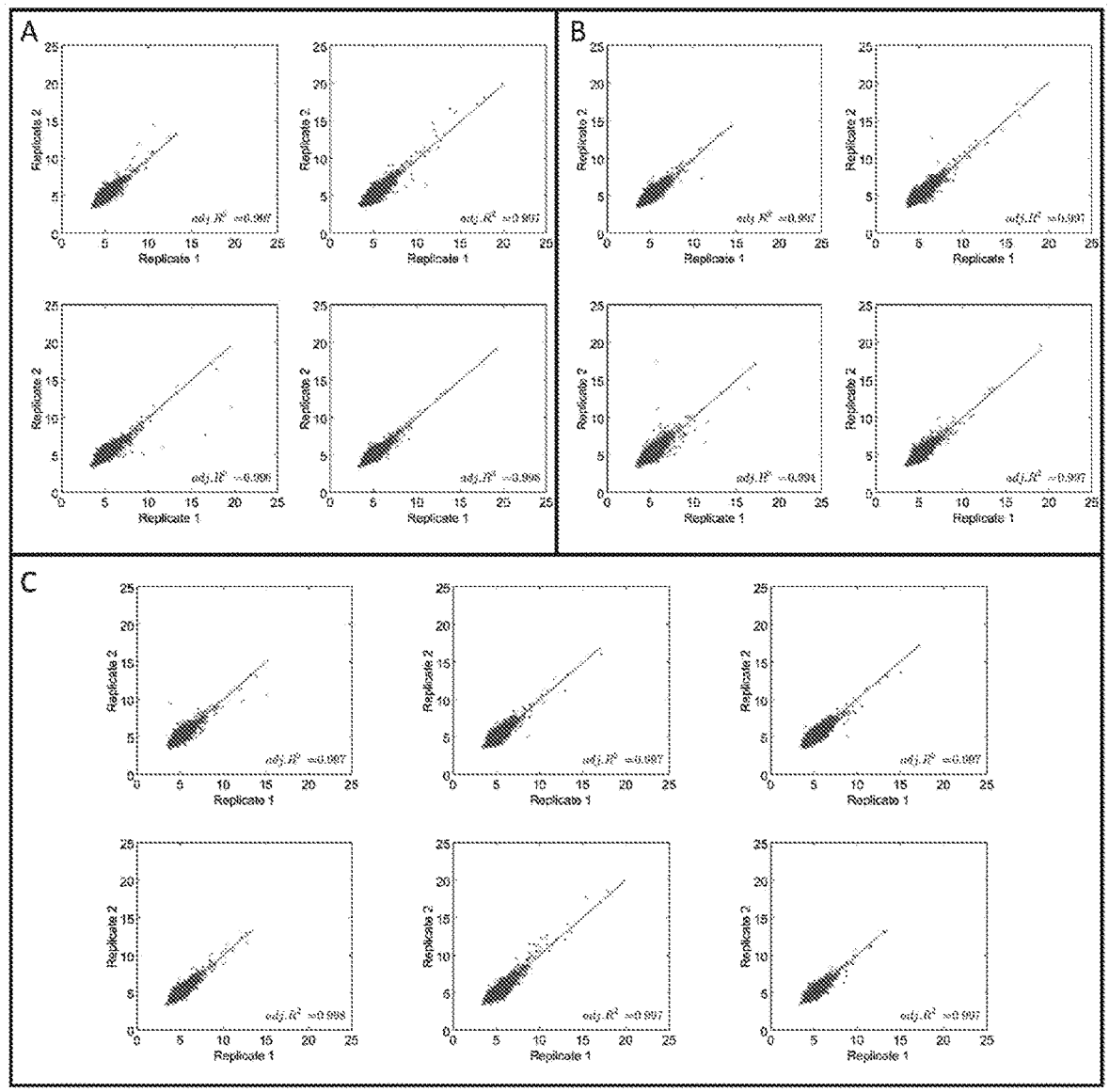

Figure 12: Extraction method to isolate human mRNA biomarkers in stool samples. A. BioAnalyzer traces for nucleic acid extraction methods described in the literature B. BioAnalyzer traces for the nucleic acid extraction method described in the invention.
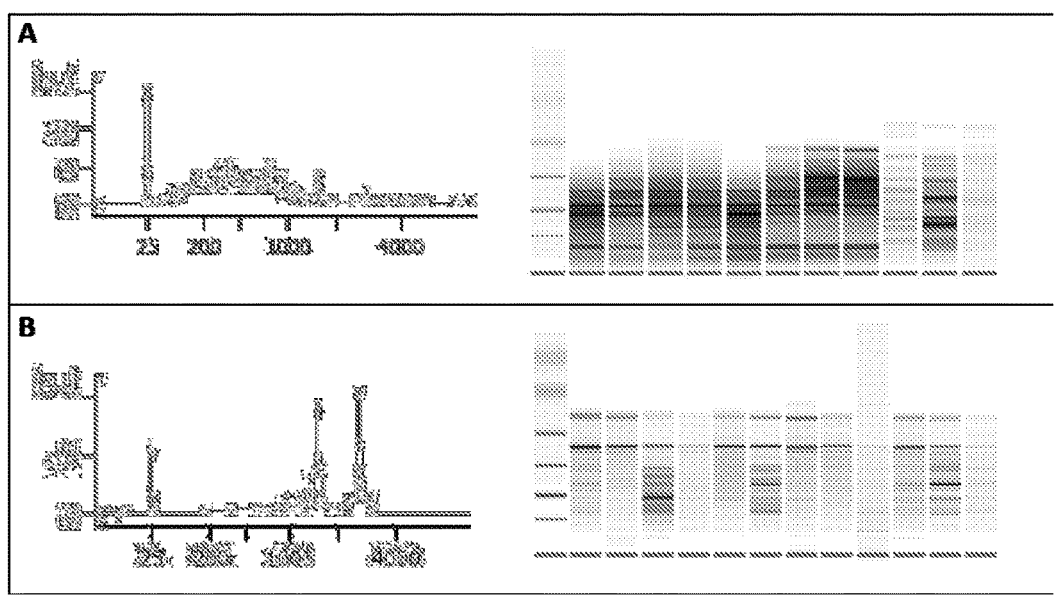

Figure 13: 400 Gene Signature for Colorectal Cancer and Precancerous Polyp Diagnosis

| | | | | | | | |
|---|---|---|---|---|---|---|---|
| ABCB1 | CD151 | DDIAS | GAST | KIF2C | NOS2 | RALGDS | TCF20 |
| ABCG2 | CD24 | DDIT3 | GDNF | KISS1R | NUP88 | RARB | TCF7 |
| ACHE | PDL1 | DHRS9 | GLI2 | KLF4 | OAS1 | RASAL2 | TCF7L2 |
| ACRBP | CD276 | DPP6 | GLRX3 | KLK4 | ODC1 | RASSF1 | TCN2 |
| ACTB | CD3D | DPYD | GNB2 | KMT2C | OGG1 | RBM47 | TDG |
| ACY1 | CD8A | DRD4 | GNG12 | KRAS | OLR1 | RFC3 | TENM1 |
| ADAMTS9 | CDC20 | DSC2 | GNG8 | KRT19 | OTX1 | RGCC | TERT |
| ADCY1 | CDC42 | DST | GOLPH3 | KRT20 | PARP1 | RHOA | TGFA |
| ADCY5 | CDC73 | EDN1 | GSN | LAMC2 | PARP11 | RNU2-1 | THBD |
| AGR2 | CDH1 | EGFR | GSTA4 | LAMP2 | PDCD1LG2 | ROCK2 | TIAM1 |
| AHNAK | CDH22 | EGLN2 | GSTM1 | LBR | PDGFA | ROR1 | TJP3 |
| AIM2 | CDHR5 | EGLN3 | GSTP1 | LDHA | PDGFRB | RPIA | TLR2 |
| AKT1 | CDK1 | EHMT2 | HDAC1 | LGR4 | PEA15 | RPL19 | TLR3 |
| AKT2 | CDK12 | ELAVL1 | HDAC11 | LGR5 | PER3 | RPLP0 | TMEFF2 |
| ALDOA | CDKN1A | ELF3 | HDAC5 | LIN28A | PGGT1B | RPRM | TMEM158 |
| ALK | CDKN2A | EMP1 | HDHD3 | LMNB2 | PIK3CB | RPS27A | TMPRSS2 |
| AMD1 | CDKN2B | EPCAM | HGF | LPCAT1 | PLA2G2A | RRAS2 | TNF |
| ANPEP | CEACAM1 | EPHA2 | HIF1A | LRP5 | PLAUR | RRM2 | TNFRSF10B |
| ANXA2P2 | CEACAM5 | EPHA7 | HIST1H2BM | LRPAP1 | PLCD1 | RTN4 | TNFRSF1A |
| APC | CEACAM6 | EPHB2 | HK1 | LTA | PLCG1 | S100A14 | TNFSF10 |
| APTX | CGN | EPOR | HK2 | LY96 | PLIN2 | SALL3 | TNFSF9 |
| AREG | CHD7 | EPS8L1 | HLA-DQB1 | MAGED4 | PLS1 | SALL4 | TNS4 |
| ARL4C | CHP1 | ERBB3 | HLA-DRB1 | MAP2K3 | PMS2 | SATB1 | TOP1 |
| ASCL1 | CHRNA7 | ERBB2IP | HMGA1 | MAPK3 | POLD1 | SCGB2A1 | TP73 |
| ATM | CIB1 | ERCC1 | HMGA2 | MDK | POLE | SCNN1A | TSPAN1 |
| ATP11A | CISH | ESR1 | HMGCR | MET | POU2F1 | SCNN1B | TSPEAR |
| ATP1B1 | CITED1 | ESR2 | HMOX1 | METAP2 | PPARGC1A | SEMA4A | TTLL3 |
| ATPIF1 | CLDN3 | ESRP1 | HOXA10 | MKI67 | PPFIBP2 | SEMG1 | TUBB3 |
| ATRX | CLDN4 | FASN | HOXA9 | MKRN3 | PPM1D | SETD2 | TXNIP |
| AURKA | CLDN7 | FBXL2 | HP | MLH1 | PPP2CB | SFN | TYMP |
| B2M | CNTN1 | FBXL20 | HRH2 | MLH3 | PPP2R1B | SFRP5 | TYMS |
| B3GNT3 | COL5A1 | FCGR3A | HSD17B1 | MNX1 | PRICKLE2 | SHROOM2 | UBA52 |
| B4GALT3 | COMT | FCN2 | HSPB6 | MPO | PRKAR1A | SKP1 | UBD |
| BAD | CREB5 | FDFT1 | ID1 | MSH5 | PROK2 | SLC12A5 | UGCG |
| BCR | CREBBP | FDPS | IFNA1 | MT-CO1 | PRSS22 | SLC25A46 | UGT2B7 |
| BIRC5 | CSF1R | FFAR4 | IFNAR1 | MTA1 | PSMB8 | SLC35F5 | UHRF1 |
| BMP3 | CSF3R | FGF4 | IGF2 | MTHFD1 | PSMD10 | SMAD7 | VEGFA |
| BRAF | CSRNP3 | FHIT | IGF2R | MUC1 | PTEN | SNX1 | VEZF1 |
| BRS3 | CST1 | FLCN | IGFBP3 | MUC2 | PTGER2 | SPATA2 | VTCN1 |
| BUB1 | CTLA4 | FNTA | IL1B | MUC6 | PTGES2 | SPINT1 | WDR49 |
| BVES | CTNNA1 | FNTB | IL1RN | MYNN | PTGS2 | SPOP | WNT3A |
| C21orf33 | CTNNB1 | FOS | IL2 | MYO18B | PTK2B | SRC | WNT6 |
| CA6 | CTNND1 | FOXA2 | IL23A | NAPSA | PTK7 | SRGN | WNT7A |
| CABLES1 | CUX1 | FOXH1 | IRF6 | NAT10 | PTPN11 | SSTR2 | WNT9A |
| CAMK2D | CXCL8 | FOXO4 | ITCH | NAT2 | PTPRS | ST14 | WRN |
| CASC2 | CXCR2 | FRMPD2 | ITGA3 | NCK1 | PTPRU | STAB1 | YY1 |
| CBLN4 | CXCR4 | FUT3 | ITGB4 | NDOR1 | PVR | STAT3 | ZNF135 |
| CCDC129 | CYCS | GADD45A | JAK1 | NEUROG1 | PYCR1 | STK11 | ZNF492 |
| CCNB1 | CYP1A1 | GAPDH | KALRN | NFIB | PYGO1 | SUZ12 | ZNF560 |
| CCNG2 | DBP | GAS5 | KIF26B | NFKBIA | RAC1 | TAC1 | ZSCAN16 |

Figure 14: BioAnalyzer Traces for biological replicates for four different feline samples. Columns one through three are from cat 'A', columns four and five are from cat 'B', column six is from cat 'C', and columns seven and eight are from cat 'D'.
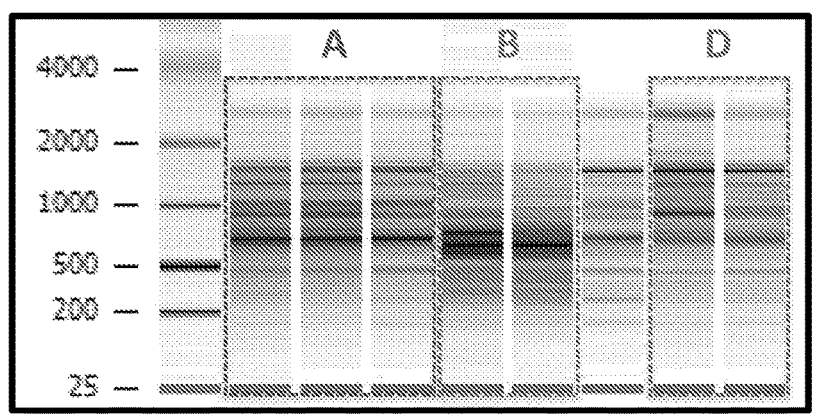

Figure 15A: Tables depicting primers designed and used for RT-qPCR of canine samples.

A

| Product Name | Target | Primer Name | Sequence (5-3') | |
|---|---|---|---|---|
| ActB | Epithelial cell positive control | ActBfwd | AGACCGCGTCCACCCCGC | (SEQ. ID NO.: 1) |
| | | ActBrev | CGAAGCCGGCCTTGCACATG | (SEQ. ID NO.: 2) |
| GAPDH | Normalization control | GDHfwd | ATGGTGAAGGTCGGAGTCAAC | (SEQ. ID NO.: 3) |
| | | GDHrev | GTGGGTAGAATCATACTGGAACA | (SEQ. ID NO.: 4) |
| IgA | IgA heavy chain conserved region | IgAfwd | AGTGACCTAGCGTGTCATTCTG | (SEQ. ID NO.: 5) |
| | | IgArev | GCTGTCTGGACCCCTTACATG | (SEQ. ID NO.: 6) |
| Cμ | IgM heavy chain | Cμ1 | TTCCCCCTCATCACCTGTGA | (SEQ. ID NO.: 7) |
| | | Cμ2 | GGTTGTTGATTGCACTGAGG | (SEQ. ID NO.: 8) |
| IgH Major | B-cell immuno globulin | IgH1 | CAGCCTGAGAGCCGAGGACAC | (SEQ. ID NO.: 9) |
| | | IgH2 | TGAGGAGACGGTGACCAGGGT | (SEQ. ID NO.: 10) |
| IgH Minor | | IgH1 | CAGCCTGAGAGCCGAGGACAC | (SEQ. ID NO.: 9) |
| | | IgH3 | GGAGGACACAAAGAGTGAGG | (SEQ. ID NO.: 11) |
| TCRγ | T-cell receptor gamma region | TCRγ3 | ACCCTGAGAATTGTGCCAGG | (SEQ. ID NO.: 12) |
| | | TCRγ2 | GTTACTATAAACCTGGTAAC | (SEQ. ID NO.: 13) |
| | | TCRγ1 | TCTGGGRTGTAYTACTGTGCTGTCTGG | (SEQ. ID NO.: 14) |

Figure 15B: Tables depicting primers designed and used for RT-qPCR of feline samples.

B

| Product Name | Target | Primer Name | Sequence (5-3') | |
|---|---|---|---|---|
| ActB | epithelial cell control | ActBfwd | GCC AAC CGT GAG AAG ATG AC | (SEQ ID. NO.: 15) |
| | | ActBrev | GGA GAA GAA CAG AAC CCT GG | (SEQ ID. NO.: 16) |
| GAPDH | normalization control | GDHfwd | CGG ATT TGG CCG TAT TGG GCG C | (SEQ ID. NO.: 17) |
| | | GDHrev | GGT GGA ATC ATA CTG GAA CAT GTA GAC CA | (SEQ ID. NO.: 18) |
| T cell receptor gamma region | V region primers | ftcrgv1-2 | GGS AGA AGA GCG ACG AGG GCG TG | (SEQ ID. NO.: 19) |
| | | ftcrgv3 | GGG CGA AGA GCG ATG AGG GAG TG | (SEQ ID. NO.: 20) |
| | | ftcrgv4 | GTA GTG AGG AGR ATG CTG GTC TG | (SEQ ID. NO.: 21) |
| | | ftcrgv5 | GGC AGA AGC ATG ACA AGG GCA TG | (SEQ ID. NO.: 22) |
| | constant region primer | feline TCR unirev | AGK TTT MYT TCA GCA ATT GAA GG | (SEQ ID. NO.: 23) |
| | J region TaqMan probes | ftcrgvj1 | [FAM] CCC TGA GCA GTG TGC CAG SAC [BHQ1] | (SEQ ID. NO.: 24) |
| | | ftcrgj2 | [CY3] GGG GGA GTT ACK ATG ASC TTA RTT CC [BHQ1] | (SEQ ID. NO.: 25) |
| | | ftcrgj3 | [JOE] ATC CAG ATC TCA GGT TTG GGA GGA GG [BHQ1] | (SEQ ID. NO.: 26) |
| B cell complementary determining region 3 | VH region primers | fCDR3f1 | CCA GGC TCC AGG GAA GGG | (SEQ ID. NO.: 27) |
| | | fCDR3f2 | TCC AGA GAC AAC GCC AAG AAC | (SEQ ID. NO.: 28) |
| | constant region primer | fel CDR3 unirev | GTT CGG RCG RCT RCT SGT TTC | (SEQ ID. NO.: 29) |
| | JH region TaqMan probes | fCDR3jh1 | [FAM] ACA CCG TCA CCA GGG CTC C [BHQ1] | (SEQ ID. NO.: 30) |
| | | fCDR3jh2 | [CY3] TGA GGA CAC TGT GAC TAT GGT TCC [BHQ1] | (SEQ ID. NO.: 31) |
| | | fCDR3jh3 | [JOE] GGA CAC CGT CAC YAK GVY TCC [BHQ1] | (SEQ ID. NO.: 32) |

Figure 16: PCR Amplification of lymphocyte related transcripts. A) RT-qPCR results for B cell rearrangement specific RNA in four canine samples. B) RT-qPCR results for T cell rearrangement specific RNA in four feline samples.
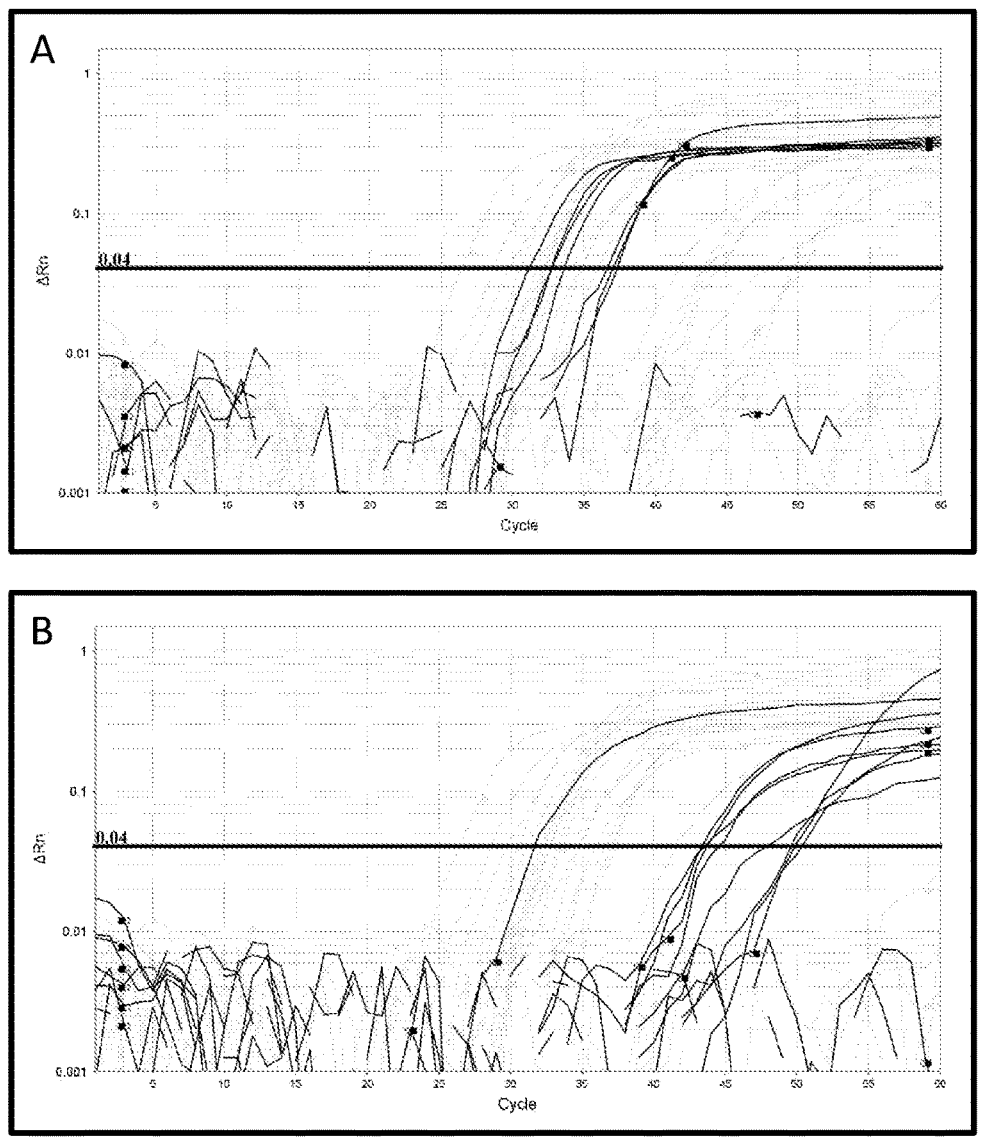

DETECTION METHOD USING EUKARYOTIC CELLS

CROSS-REFERENCE TO RELATED APPLICATIONS

This application is a U.S. national phase application filed under 35 U.S.C. § 371 of International Application No. PCT/US2017/058789, which was filed on Oct. 27, 2017, and which claims the benefit of the filing dates of U.S. Provisional Application Ser. No. 62/413,708, filed Oct. 27, 2016, U.S. Provisional Application Ser. No. 62/523,511, filed Jun. 22, 2017, and U.S. Provisional Application Ser. No. 62/547,046, filed Aug. 17, 2017, the disclosures of which are herein expressly incorporated by reference in their entirety.

FIELD OF THE INVENTION

The present invention relates to the extraction of eukaryotic nucleic acids from stool samples and the use of the nucleic acids for diagnosis and treatment of intestinal disease.

BACKGROUND

Gastrointestinal disorders, for example gastrointestinal cancer and other digestive diseases such as inflammatory bowel disease, irritable bowel syndrome, and Crohn's disease are widespread. In the US, gastrointestinal disorders are estimated to affect 60 to 70 million people annually. For some disorders, early screening and diagnosis has resulted in a reduction in mortality rates and improved quality of life for the patients. However, standard methods of diagnosis, such as colonoscopy, are invasive, time-consuming, and are associated with relatively high costs. Gastrointestinal disorders can also affect animals, for example, animals kept as pets, such as cats and dogs. Veterinary methods of screening for such disorders are similarly invasive and costly. There is a continuing need for noninvasive methods of diagnosing gastrointestinal disorders in both humans and animals.

SUMMARY

Provided herein are materials and methods for isolating eukaryotic nucleic acid from a stool sample. The method can include the steps of mixing the sample with a buffer, a surfactant and a ribonuclease inhibitor to form a suspension; separating the suspension into a portion enriched for eukaryotic cells and a portion enriched for bacterial cells and retaining the portion enriched for eukaryotic cells; adding a chaotropic agent and optionally a surfactant to the portion enriched for eukaryotic cells to form a lysate; fractioning the lysate into a cell debris layer, a layer comprising eukaryotic nucleic acids and a lipid layer; and collecting the layer comprising eukaryotic nucleic acids and optionally the lipid layer. The stool sample can be a human or non-human animal stool sample. In some embodiments, the nonhuman animal stool sample can be a sample obtained from a dog or a cat. The method can further include extracting the eukaryotic nucleic acids from the collected layer comprising eukaryotic nucleic acids. The nucleic acid can include DNA, RNA, total RNA, mRNA, tRNA, rRNA, ncRNA, smRNA, or sno RNA, or a combination of any of DNA, RNA, total RNA, mRNA, tRNA, rRNA, ncRNA, smRNA, or sno RNA.

Also provided are materials and methods for detecting a eukaryotic biomarker in a stool sample. The method can include the steps of analyzing the extracted nucleic acid by microarray sequencing, molecular barcoding, probe capture, polymerase chain reaction (PCR), ddPCR, RT-PCR, RT-qPCR, or nucleic acid sequencing. In some embodiments, the eukaryotic biomarker is selected from the biomarkers listed in FIG. 6 (Panel A) or FIG. 13 (Panel B). In some embodiments, the eukaryotic biomarker can be a B cell marker, a T cell marker, or an immunoglobulin.

Also provided are materials and methods for determining whether a subject is at risk for colorectal cancer. The method can include the steps of measuring the level of expression of two or more colorectal neoplasm biomarker genes selected from any of the colorectal neoplasm biomarker genes listed in FIG. 6 (Panel A) or FIG. 13 (Panel B) in a biological sample from the subject; comparing the measured expression level of the two or more colorectal neoplasm biomarker genes in the sample with the measured expression level of the two or more colorectal neoplasm biomarker genes in a control, wherein a difference in the measured expression level of the two or more genes in the biological sample relative to the measured expression level of the two or more genes in the control indicates that the subject is at risk for colorectal cancer. In some embodiments, the colorectal neoplasm biomarker genes can be contained within the 200 differentially expressed transcript clusters shown in FIG. 5A and contained within the common pathways associated with colorectal cancer shown in FIG. 5B. In some embodiments, the colorectal neoplasm biomarker gene can be selected from the biomarkers listed in FIG. 6 (Panel A) or FIG. 13 (Panel B).

Also provided are materials and methods for a clinical plan for a subject having or at risk for colorectal cancer. The method can include the steps of: measuring the level of expression of two or more colorectal neoplasm biomarker genes selected from any of the colorectal neoplasm biomarker genes listed in FIG. 6 (Panel A) or FIG. 13 (Panel B) in a biological sample from the subject; comparing the measured expression level of the two or more colorectal neoplasm biomarker genes in the sample with the measured expression level of the two or more colorectal neoplasm biomarker genes in a control, wherein a difference in the measured expression level of the two or more genes relative to the measured expression level of the two or more genes in the control indicates that the subject has or is at risk for colorectal cancer; and selecting a clinical plan based on the a difference in the measured expression level of the two or more genes relative to the measured expression level of the two or more genes in the control indicates that the subject has or is at risk for colorectal cancer.

Also provided are methods and compositions for determining whether a nonhuman animal is at risk for a gastrointestinal disorder. The method can include the steps of measuring the level of expression of one or more B cell, T cell, or immunoglobulin genes in a biological sample from the subject; comparing the measured expression level of the one or more B cell, T cell, or immunoglobulin genes in the sample with the measured expression level of one or more B cell, T cell, or immunoglobulin genes in a control, wherein a difference in the measured expression level of the one or more genes in the biological sample relative to the measured expression level of the one or more genes in the control indicates that the subject is at risk for a gastrointestinal disorder. The gastrointestinal disorder can be gastrointestinal lymphoma or inflammatory bowel disease. The nonhuman animal can be a cat or a dog. The biological sample can be a stool sample.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein:

FIG. 1 is an electrophoresis file run. The electrophoretic analysis was used to check the quality of the extracted RNA.

FIG. 2 is an electropherogram. The electropherogram was used to check the quality of the extracted RNA.

FIG. 3 is an extraction summary. This depicts a summary of quality check for 120 samples that were evaluated using the extraction method described in Example 2.

FIG. 4A is a graph depicting the results of an experiment comparing total RNA extraction methods. FIG. 4A shows the total number of samples passing quality check using the extraction method described in Example 2.

FIG. 4B depicts five electrophoresis runs from various extraction methods

FIG. 5A is a heat map showing differentially expressed transcript clusters. As shown, a heat map was generated using 200 transcript clusters, which were mapped to 187 different genes, and the 265 samples analyzed in the training set. Samples are ordered by groups: cancer (red), precancerous adenoma (orange), and normal (green).

FIG. 5B shows differentially expressed GO terms and pathways using GAGE R-Package (p<0.05). The height of each bar details the set size of enriched genes within each pathway and the blue line shows the −log(p-value) for each pathway. The red dotted line indicates significance (p=0.05).

FIG. 6 shows a listing of genes identified as differentially expressed in colorectal neoplasms.

FIG. 7A depicts an electrophoresis run showing 4 individual feline samples and 4 individual canine samples.

FIG. 7B shows the RNA Integrity Numbers (RIN) for 4 individual feline samples and 4 individual canine samples and the average of all eight samples.

FIG. 7C shows estimated eukaryotic RNA concentration (ng/uL) from an electrophoresis run, for 4 individual feline samples and 4 individual canine samples and the average mass for all 8 samples.

FIG. 8A depicts RT-qPCR results for the IgM Cμ heavy chain region to identify the presence of lymphocyte related transcripts in canine samples.

FIG. 8B depicts RT-qPCR results for two recombinations of the T cell receptor gamma region in canine samples.

FIG. 9 depicts RT-qPCR results for Actin-B in feline samples.

FIG. 10A depicts 4 technical replicates of 70,524 transcript cluster expression levels using Affymetrix Human Transcriptome Arrays.

FIG. 10B depicts 4 biological replicates of 70,524 transcript cluster expression levels using Affymetrix Human Transcriptome Arrays.

FIG. 10C depicts 6 technical replicates tested 6 months apart to analyze 70,524 transcript cluster expression levels using Affymetrix Human Transcriptome Arrays.

FIG. 11A depicts 4 technical replicates of 5,149 transcript cluster expression levels using Affymetrix Human Transcriptome Arrays.

FIG. 11B depicts 4 biological replicates of 5,149 transcript cluster expression levels using Affymetrix Human Transcriptome Arrays.

FIG. 11C depicts 6 technical replicates tested 6 months apart to analyze 5,149 transcript cluster expression levels using Affymetrix Human Transcriptome Arrays.

FIG. 12A depicts a comparative electropherogram and electrophoresis file run from extraction methods in the literature.

FIG. 12B depicts an electropherogram and an electrophoresis file run from extraction methods described in Example 2.

FIG. 13 shows a listing of genes identified as differentially expressed in colorectal neoplasms, as well as genes implicated in cancer, colorectal neoplasms and/or gastrointestinal health.

FIG. 14 depicts an electrophoresis file run for 8 samples derived from 4 individual cats demonstrating the consistency of eukaryotic and prokaryotic RNA signatures among biological replicates.

FIG. 15A is a table showing primers used for RT-qPCR analysis of canine samples.

FIG. 15B is a table showing primers used for RT-qPCR analysis of feline samples.

FIG. 16A depicts RT-qPCR results for two rearrangements of B-cell immunoglobulins to identify the presence of lymphocyte-specific transcripts in canine samples.

FIG. 16B depicts RT-qPCR results for the six rearrangements of the T-cell receptor gamma region to identify the presence of lymphocyte-specific transcripts in feline samples.

DETAILED DESCRIPTION

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship. When only a single machine is illustrated, the term "machine" shall also be taken to include any collection of machines that individually or jointly execute a set (or multiple sets) of instructions to perform any one or more of the methodologies discussed herein. In the claims, means-plus-function clauses, if used, are intended to cover the structures described, suggested, or rendered obvious by the written description or drawings for performing the recited function, including not only structural equivalents but also equivalent structures.

The present invention is based in part on the inventors' development of a method to separate eukaryotic cells from bacterial cells in a stool sample, for example, a stool sample obtained from a mammal. Within the colon, there are about approximately $10^{12}$ bacterial cells per gram of intestinal content. This colonic microflora can include between 300-

1000 species. A stool or fecal sample is a complex macromolecular mixture that includes not only eukaryotic cells sloughed off from the intestinal lumen of the gastrointestinal tract, but microbes, including bacteria and any gastrointestinal parasites, indigestible unabsorbed food residues, secretions from intestinal cells, and excreted material such as mucous and pigments. Normal stool is made up of about 75% water and 25% solid matter. Bacteria make up about 60% of the total dry mass of feces. The high bacterial load can contribute to an unfavorable signal-to-noise ratio for the detection of eukaryotic biomarkers from a stool sample. Furthermore, the eukaryotic signals can be heavily degraded. Extraction and processing of such eukaryotic nucleic acids can promote or accelerate degradation, which severely limits further analysis.

The methods and materials disclosed herein include methods for isolating eukaryotic nucleic acids from a stool sample. Such eukaryotic nucleic acids can be evaluated for levels of specific biomarkers that may be indicative of a gastrointestinal disorder or disease in a eukaryote, for example, a mammal. The mammal can be a human or a non-human animal, for example, a human, dog, cat, non-human primate, ruminant, ursid, equid, pig, sheep, goat, camelid, buffalo, deer, elk, moose, mustelid, rabbit, guinea pig, hamster, rat, mouse, pachyderm, rhinoceros, or chinchilla.

The inventors have found that that they could effectively separate eukaryotic cells from bacterial cells in a eukaryotic stool sample. The inventors have also found that they could detect eukaryotic biomarkers in the RNA isolated from such eukaryotic cells. Such biomarkers may be useful for the detection of gastrointestinal disorders, for example, colorectal cancer, celiac disease, Crohn's disease, gastritis, gastroenteritis, gastric cancer, gastric ulcers, necrotizing enterocolitis, gastrointestinal stromal tumors, gastrointestinal lymphoma, gastrointestinal neoplasia, lymphosarcoma, adenocarcinoma, inflammatory bowel disease, irritable bowel syndrome, pancreatic neoplasia, hepatic neoplasia, cholangiocarcinoma, colitis, feline leukemia virus, bovine viral diarrhea, jejunal hemorrhage syndrome, gastroenteritis, malignant catarrhal fever, feline panleukopenia, small intestinal fibrosis, infiltrative colonic disease, cryptosporidiosis, coccidiosis, and other zoonotic parasitic infections, or coronavirus, parvovirus, astrovirus, norovirus, or rotavirus infections. Provided herein are materials and methods for determining whether a subject, for example, a human, a dog or a cat, is at risk for gastrointestinal disease, for example, colorectal cancer, lymphoma or inflammatory bowel disease or other diseases. Also provided are materials and methods for diagnosis of disease and methods of identifying the health status of a subject.

The methods and compositions disclosed herein are generally and variously useful for the detection, diagnosis, and treatment of gastrointestinal health. Methods of detection can include measuring the expression level in a stool sample of one, two, or more biomarkers in a sample from a subject, for example, a patient, having a gastrointestinal disorder or suspected of having a gastrointestinal disorder and comparing the measured expression level to the measured expression level of one, two, or more biomarkers in a control. A difference in the measured expression level of one, two, or more biomarkers in a subject's sample relative to the measured expression level of the one, two, or more biomarkers in a control is an indication that the subject has a gastrointestinal disorder. In some embodiments, a difference in the measured expression level of one, two, or more biomarkers in a subject's sample relative to the measured expression level of the one, two, or more biomarkers in a control is an indication that the subject, for example, a patient, is at risk for a gastrointestinal disorder.

In another embodiment, methods of detection of disease can include measuring the relative expression level proportion, for example, the relative ratios, of one, two, or more biomarkers in a subject's stool sample and comparing the relative proportion of these biomarkers to the relative expression level proportion of one, two, or more biomarkers in a control. A difference in the measured relative expression level proportion of one, two, or more biomarkers in a subject's sample relative to a control is an indication that the subject has a gastrointestinal disease. In some embodiments, a difference in the measured expression level proportion of the one, two, or more biomarkers in a subject's sample relative to the measured expression level proportion of the one, two, or more biomarkers in a control is an indication that the subject is at risk for a gastrointestinal disorder.

The methods can include determining the level of expression of two or more colorectal neoplasm biomarkers in the human RNA isolated from a stool sample obtained from a patient by determining whether the levels of the two or more colorectal neoplasm biomarker genes are different relative to the levels of the same two or more colorectal neoplasm biomarker genes in a control. Exemplary colorectal neoplasm biomarker genes are shown in FIG. 6 (Panel A) and FIG. 13 (Panel B). Some or all of the colorectal neoplasm biomarker genes listed in FIG. 6 (Panel A) and FIG. 13 (Panel B) can form a panel. In some embodiments, the colorectal neoplasm biomarker genes listed in FIG. 6 (Panel A) and FIG. 13 (Panel B) can also include subsets of colorectal neoplasm biomarker genes. The compositions can include gene arrays and probe sets configured for the specific detection of the panels of markers disclosed herein. The compositions can also include kits comprising gene arrays and probe sets configured for the specific detection of the panels of markers disclosed herein.

Provided herein are colorectal neoplasm biomarker genes and panels of colorectal neoplasm biomarker genes for use in diagnosis of colorectal cancer or precancerous lesions. A biomarker is generally a characteristic that can be objectively measured and quantified and used to evaluate a biological process, for example, colorectal neoplasm development, progression, remission, and recurrence. Biomarkers can take many forms including, nucleic acids, polypeptides, metabolites, or physical or physiological parameters.

These biomarkers from eukaryotic cells can include: a) a sequence of deoxyribonucleic acid (DNA), b) a sequence of ribonucleic acid (RNA), c) a predicted sequence of amino acids, which comprise the backbone of protein, d) expression levels of ribonucleic acid biomarkers, e) a predicted expression level of an amino acid sequence or f) any combination of the above. In some embodiments, the biomarker can be T cell marker or B cell marker. In some embodiments, the biomarker can be a biomarker that is useful for the detection of clonal expansion of T cells or B cells. Exemplary biomarkers can include IgA, IgM, IgG, IgE, IgD, T cell gamma receptor, T cell alpha receptor, T cell beta receptor, the T cell delta receptor region, or B-cell complementary determining region. In some embodiments, biomarkers can be used for normalization, such as GADPH. In some embodiments, biomarkers can be used for detection of specific cell types, such as using Actin-B for the detection of epithelial cells or IgM C-mu for the detection of lymphocytes. In some embodiments, biomarkers can be used for detection of disease specific markers, such as detection of T cell receptor gamma for detection of clonal expansion of lymphocytes. In some embodiments, biomarkers can comprise those for the detection of viruses and parasites, including those for capsids, capsomeres, replicases, and oocyst wall proteins.

A biological sample can be a sample that contains cells or other cellular material from which nucleic acids or other analytes can be obtained. A biological sample can be a control or an experimental sample. A biological sample can be a stool sample. The biological sample can be obtained immediately following defecation in a toilet, on the ground, or into a collection device. In some embodiments, the biological sample can be obtained following a procedure, such as an enema or an endoscopy. The biological sample can be tested immediately. Alternatively, the biological sample can be stored in a buffer prior to testing, for example an aqueous buffer, a glycerol based buffer, a polar solvent based buffer, an osmotic balance buffer, or other buffer sufficient for preserving the biological sample. Additionally, or alternatively, the biological sample can be collected and stored refrigerated, for example, at 4° C., or frozen, for example, at 0° C., −20° C., −80° C., −140° C., or lower prior to testing. The biological sample can be stored for 1 month, 2 months, 4 months, 6 months, 1 year, 2 years or more prior to testing.

The biological sample can be derived from a eukaryote, for example a mammal. The mammal can be a human or a non-human animal, for example, a human, dog, cat, non-human primate, ruminant, ursid, equid, pig, sheep, goat, camelid, buffalo, deer, elk, moose, mustelid, rabbit, guinea pig, hamster, rat, mouse, pachyderm, rhinoceros, or chinchilla.

Methods

Useful methods for isolation of nucleic acids from a biological sample, for example a stool sample, that are enriched for eukaryotic nucleic acids are provided herein. The method can include disrupting the stool sample with buffer. The sample can be subjected to vortexing, shaking, stirring, rotation, or other method of agitation sufficient to disperse the solids and the stool bacteria. The temperature at which the agitation and centrifugation steps are carried out can vary, for example, from about 4° C. to about 20° C., from about 4° C. to about 1° C., from about 4° C. to about 10° C., from about 4° C. to about 6° C. Following disruption, the sample can be subjected to one or more rounds of centrifugation. In some embodiments, the disruption step and the centrifugation can be repeated one, two, three, or more additional times. Commercially available reagents, for example Nuclisens® EasyMag® reagents can be used for stool disruption, washing, and cell lysis. Lysis buffer can also be to lyse the eukaryotic cells. The lysate can be further centrifuged and the supernatant used for input into an automated RNA isolation machine, for example EasyMag® instrument. In some embodiments, the extracted nucleic acids can be treated with DNase to clear the solution of DNA. Other methods can be used including mechanical or enzymatic cell disruption followed by a solid phase method such as column chromatography or extraction with organic solvents, for example, phenol-chloroform or thiocyanate-phenol-chloroform extraction. In some embodiments, the nucleic acid can be extracted onto a functionalized bead. In some embodiments, the functionalized bead can further comprise a magnetic core ("magnetic bead"). In some embodiments, the functionalized bead can include a surface functionalized with a charged moiety. The charged moiety can be selected from: amine, carboxylic acid, carboxylate, quaternary amine, sulfate, sulfonate, or phosphate.

For extraction of nucleic acids, the stool sample can be disrupted in the presence of one or more of a buffer, a surfactant, and a ribonuclease inhibitor to form a suspension. The buffer can be a biologically compatible buffer, for example, Hanks balanced salt solution, Alsever's solution, Earle's balanced salt solution, Gey's balanced salt solution, Phosphate buffered saline, Puck's balanced salt solution, Ringer's balanced salt solution, Simm's balanced salt solution, TRIS-buffered saline, or Tyrode's balanced salt solution. The surfactant can be an ionic or non-ionic surfactant, for example, Tween-20, or Triton-X-100. The ribonuclease inhibitor can be solvent based, protein based, or other type of method to prevent RNA destruction, including, for example, Protector RNase Inhibitor (Roche), RNasin® (Promega), SUPERase-In™ (Thermo Fisher Scientific), RNAse-OUT™ (Thermo Fisher Scientific), ANTI-RNase, Recombinant RNase Inhibitor, or a cloned RNAse Inhibitor. The stool sample can be disrupted in a variety of ways, for example by vortexing, shaking, stirring, rotating, or other method of agitation sufficient to disperse the solids and the stool bacteria. In some embodiments, the stool sample can be disrupted using: coated beads, magnetic beads, or a stirring implement, such as a glass rod, a metal rod, a wooden stick or a wooden blade.

The suspension can then be separated into a liquid portion and a solid portion. The separation can be carried out, for example, by centrifugation, filtration, targeted probes that specifically bind eukaryotic cells, antibodies, column-based filtration, bead-based filtration, or chromatographic methods. The liquid portion is enriched for bacterial nucleic acid and can be discarded. The solid portion can be re-suspended in a buffer either in the presence or absence of a surfactant and in the presence or absence of a ribonuclease. The separation step can be repeated one, two, three, four, five, six, seven, eight, or more times.

The temperature at which the disruption and separation steps are carried out can vary, for example, from about 4° C. to about 20° C., from about 4° C. to about 15° C., from about 4° C. to about 10° C., from about 4° C. to about 6° C.

The resulting pellet obtained from the separation step can be suspended in a lysis buffer, for example, a buffer comprising a chaotropic agent and optionally a surfactant to form a lysate. In some embodiments, the chaotropic agent can be guanidium thiocyanate and the surfactant can be Triton-X-100. In some embodiments, the lysis buffer can include or exclude Tris-HCl, ethylenediaminetetraacetic acid (EDTA), sodium dodecyl sulfate (SDS), Nonidet P-40, sodium deoxycholate, or dithiothreitol.

The lysate can be fractionated into a portion enriched for eukaryotic nucleic acid. The fractionation can be carried out, for example by centrifugation, filtration, targeted probes that specifically bind eukaryotic nucleic acid, antibodies, column-based filtration, bead-based filtration, or chromatographic methods. In some embodiments, fractionation by centrifugation can result in the formation of a bottom layer (a pellet), comprising cell debris, a hydrophilic middle layer comprising eukaryotic nucleic acids, and a hydrophobic top layer comprising lipids and membrane fractions. The middle layer can be collected. In some embodiments, the middle layer and the top layer can be collected together. The middle layer can be collected through a narrow bore orifice. The narrow bore orifice can be a pipette tip or a syringe fitted with a needle. The pipette tip can be, for example, a 1, 5, 10, 20 uL or 100 uL pipette tip. The needle can be, for example, an 18-gauge or a 15-gauge needle.

The collected layer comprising eukaryotic nucleic acids can be subjected to further extraction. The method of further extraction can vary. Exemplary methods include magnetic particle-based methods, column based methods, filter-based methods, bead-based methods, or organic solvent-based methods. Magnetic particle-based methods can include commercially available reagents, for example Nuclisens® Easy-Mag® reagents (bioMerieux).

The extracted nucleic acids can be analyzed for eukaryotic biomarkers that are relevant to gastrointestinal disorders or gastrointestinal cells. The biomarkers can provide information on the health of an individual, i.e., the subject. These biomarkers from eukaryotic cells can include: a) a sequence of deoxyribonucleic acid (DNA), b) a sequence of ribonucleic acid (RNA), c) a predicted sequence of amino acids, which comprise the backbone of protein, d) expression levels or proportions of expression levels of RNA biomarkers, e) a predicted expression level or a predicted expression level proportion of an amino acid sequence, or f) any combination of the above. Isolation of biomarkers from eukaryotic cells can allow for comparison between an experimental sample and a control. Isolation of these biomarkers from eukaryotic cells can provide a method for detection of intestinal disease in the experimental sample. Comparison can include evaluation for: a) variation in a DNA sequence, b) variation in an RNA sequence, c) variation in the predicted amino acid sequence, d) variation in expression levels or the variation of the proportion of expression levels of RNA biomarkers, e) variation in the predicted expression level or variation in the prediction expression level proportion of an amino acid sequence, or f) a variation constituting any combination of the above. A variation can be determined when the measured biomarker of an experimental sample is different from the measured biomarker in a control.

The method can include obtaining an experimental sample and a control, for example, a stool sample. The stool sample contains sloughed off eukaryotic cells that can be evaluated for biomarkers. In some embodiments, the eukaryotic cells can be enterocytes, lymphocytes, enterochromiffin-like cells, entero-endocrine cells, neuro-endocrine cells, pancreatic cells, hepatic cells, gastric cells, or others. The method provides a way whereby the eukaryotic cells in the stool sample can be evaluated for eukaryotic biomarkers. The biomarkers can include a sequence of DNA, a sequence of RNA, a predicted sequence of amino acids, an expression level or proportion of expression level of RNA biomarkers, a predicted expression level or a predicted expression level proportion of an amino acid sequence or any combination of the above. In one aspect, the evaluation step comprises of any type of microarray sequencing, polymerase chain reaction (PCR), nucleic acid sequencing, molecular barcoding, or probe-capture.

The methods and compositions are also useful for selecting a clinical plan for an individual suffering from intestinal disease. Through this method, the clinical plan can include administration of further diagnostic procedures. In some embodiments, the clinical plan can include a method of treatment.

The levels of the eukaryotic biomarkers can be evaluated using a variety of methods. Expression levels can be determined either at the nucleic acid level, for example, the RNA level or at the polypeptide level. RNA expression can encompass expression of total RNA, mRNA, tRNA, rRNA, ncRNA, smRNA, miRNA, and snoRNA. Expression at the RNA level can be measured directly or indirectly by measuring levels of cDNA corresponding to the relevant RNA. Alternatively, or in addition, polypeptides encoded by the RNA, RNA regulators of the genes encoding the relevant transcription factors, and levels of the transcription factor polypeptides can also be assayed. Methods for determining gene expression at the mRNA level include, for example, microarray analysis, serial analysis of gene expression (SAGE), RT-PCR, blotting, hybridization based on digital barcode quantification assays, multiplex RT-PCR, digital drop PCR (ddPCR), NanoDrop spectrophotometers, RT-qPCR, qPCR, UV spectroscopy, RNA sequencing, next-generation sequencing, lysate based hybridization assays utilizing branched DNA signal amplification such as the QuantiGene 2.0 Single Plex, and branched DNA analysis methods. Digital barcode quantification assays can include the BeadArray (Illumina), the xMAP systems (Luminex), the nCounter (Nanostring), the High Throughput Genomics (HTG) molecular, BioMark (Fluidigm), or the Wafergen microarray. Assays can include DASL (I lumina), RNA-Seq (Illumina), TruSeq (Illumina), SureSelect (Agilent), Bioanalyzer (Agilent) and TaqMan (ThermoFisher).

We may use the terms "nucleic acid" and "polynucleotide" interchangeably to refer to both RNA and DNA, including cDNA, genomic DNA, synthetic DNA, and DNA (or RNA) containing nucleic acid analogs, any of which may encode a polypeptide of the invention and all of which are encompassed by the invention. Polynucleotides can have essentially any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA) and portions thereof, transfer RNA, micro RNA, ribosomal RNA, siRNA, microRNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. In the context of the present invention, nucleic acids can encode a fragment of a biomarker, for example, a biomarker for B cell or T cell clonal expansion, or a biologically active variant thereof.

An "isolated" nucleic acid can be, for example, a DNA molecule or a fragment thereof, provided that at least one of the nucleic acid sequences normally found immediately flanking that DNA molecule in a genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among many (e.g., dozens, or hundreds to millions) of other nucleic acids within, for example, cDNA libraries or genomic libraries, or gel slices containing a genomic DNA restriction digest, is not an isolated nucleic acid.

Isolated nucleic acid molecules can be produced in a variety of ways. For example, polymerase chain reaction (PCR) techniques can be used to obtain an isolated nucleic acid containing a nucleotide sequence described herein, including nucleotide sequences encoding a polypeptide described herein. PCR can be used to amplify specific sequences from DNA as well as RNA, including sequences from total genomic DNA or total cellular RNA. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Two nucleic acids or the polypeptides they encode may be described as having a certain degree of identity to one another. For example, a colorectal neoplasm biomarker gene selected from FIG. 6 (Panel A) or FIG. 13 (Panel B) and a biologically active variant thereof may be described as exhibiting a certain degree of identity. Alignments may be assembled by locating short sequences in the Protein Information Research (PIR) site, followed by analysis with the "short nearly identical sequences" Basic Local Alignment Search Tool (BLAST) algorithm on the NCBI website.

As used herein, the term "percent sequence identity" refers to the degree of identity between any given query sequence and a subject sequence. For example, a colorectal neoplasm biomarker gene sequence listed in FIG. 6 (Panel A) or FIG. 13 (Panel B) can be the query sequence and a fragment of a colorectal neoplasm biomarker gene sequence listed in FIG. 6 (Panel A) or FIG. 13 (Panel B) can be the subject sequence. Similarly, a fragment of a colorectal neoplasm biomarker gene sequence listed in FIG. 6 (Panel A) or FIG. 13 (Panel B) can be the query sequence and a biologically active variant thereof can be the subject sequence.

To determine sequence identity, a query nucleic acid or amino acid sequence can be aligned to one or more subject nucleic acid or amino acid sequences, respectively, using a computer program, for example, ClustalW (version 1.83, default parameters), which allows alignments of nucleic acid or protein sequences to be carried out across their entire length (global alignment).

The nucleic acids and polypeptides described herein may be referred to as "exogenous". The term "exogenous" indicates that the nucleic acid or polypeptide is part of, or encoded by, a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the native sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

Nucleic acids of the invention can include nucleic acids having a nucleotide sequence of any one of the colorectal neoplasm biomarkers listed in FIG. 6 (Panel A) or FIG. 13 (Panel B), or a nucleic acid sequence that is at least about 70%, at least about 75%, at least about 80%, at least about 85%, at least about 90%, at least about 95%, at least about 99% identical to the nucleic acids listed in FIG. 6 (Panel A) or FIG. 13 (Panel B).

A nucleic acid, for example, an oligonucleotide (e.g., a probe or a primer) that is specific for a target nucleic acid will hybridize to the target nucleic acid under suitable conditions. We may refer to hybridization or hybridizing as the process by which an oligonucleotide single strand anneals with a complementary strand through base pairing under defined hybridization conditions. It is a specific, i.e., non-random, interaction between two complementary polynucleotides. Hybridization and the strength of hybridization (i.e., the strength of the association between the nucleic acids) is influenced by such factors as the degree of complementary between the nucleic acids, stringency of the conditions involved, and the melting temperature (Tm) of the formed hybrid. The hybridization products can be duplexes or triplexes formed with targets in solution or on solid supports.

In some embodiments, the nucleic acids can include short nucleic acid sequences useful for analysis and quantification of the colorectal neoplasm biomarker genes listed in FIG. 6 or 13. Such isolated nucleic acids can be oligonucleotide primers. In general, an oligonucleotide primer is an oligonucleotide complementary to a target nucleotide sequence, for example, the nucleotide sequence of any of the colorectal neoplasm biomarker genes listed in FIG. 6 or 13, that can serve as a starting point for DNA synthesis by the addition of nucleotides to the 3' end of the primer in the presence of a DNA or RNA polymerase. The 3' nucleotide of the primer should generally be identical to the target sequence at a corresponding nucleotide position for optimal extension and/or amplification. Primers can take many forms, including for example, peptide nucleic acid primers, locked nucleic acid primers, unlocked nucleic acid primers, and/or phosphorothioate modified primers. In some embodiments, a forward primer can be a primer that is complementary to the anti-sense strand of dsDNA and a reverse primer can be a primer that is complementary to the sense-strand of dsDNA. We may also refer to primer pairs. In some embodiments, a 5' target primer pair can be a primer pair that includes at least one forward primer and at least one reverse primer that amplifies the 5' region of a target nucleotide sequence. In some embodiments, a 3' target primer pair can be a primer pair at least one forward primer and at least one reverse primer that amplifies the 3' region of a target nucleotide sequence. In some embodiments, the primer can include a detectable label, as discussed below. In some embodiments, the detectable label can be a quantifiable label.

Oligonucleotide primers provided herein are useful for amplification of any of the colorectal neoplasm biomarker gene sequences listed in FIG. 6 (Panel A) or FIG. 13 (Panel B). In some embodiments, oligonucleotide primers can be complementary to two or more of the colorectal neoplasm biomarker genes disclosed herein, for example, the colorectal neoplasm biomarker genes listed in FIG. 6 (Panel A) or FIG. 13 (Panel B). The primer length can vary depending upon the nucleotide base sequence and composition of the particular nucleic acid sequence of the probe and the specific method for which the probe is used. In general, useful primer lengths can be about 8, 9, 10, 11, 12, 13, 14, 15, 16, 17, 18, 19, 20, 21, 22, 23, 24, 25, 26, 27, 28, 29, 30 nucleotide bases. Useful primer lengths can range from 8 nucleotide bases to about 60 nucleotide bases; from about 12 nucleotide bases to about 50 nucleotide bases; from about 12 nucleotide bases to about 45 nucleotide bases; from about 12 nucleotide bases to about 40 nucleotide bases; from about 12 nucleotide bases to about 35 nucleotide bases; from about 15 nucleotide bases to about 40 nucleotide bases; from about 15 nucleotide bases to about 35 nucleotide bases; from about 18 nucleotide bases to about 50 nucleotide bases; from about 18 nucleotide bases to about 40 nucleotide bases; from about 18 nucleotide bases to about 35 nucleotide bases; from about 18 nucleotide bases to about 30 nucleotide bases; from about 20 nucleotide bases to about 30 nucleotide bases; from about 20 nucleotide bases to about 25 nucleotide bases.

Also provided are probes, that is, isolated nucleic acid fragments that selectively bind to and are complementary to any of the colorectal neoplasm biomarker gene sequences listed in FIG. 6 (Panel A) and FIG. 13 (Panel B). Probes can be oligonucleotides or polynucleotides, DNA or RNA, single- or double-stranded, and natural or modified, either in the nucleotide bases or in the backbone. Probes can be produced by a variety of methods including chemical or enzymatic synthesis.

The probe length can vary depending upon the nucleotide base sequence and composition of the particular nucleic acid sequence of the probe and the specific method for which the probe is used. In general, useful probe lengths can be about 8, 9, 10, 11, 12, 13, 14, 15, 16, 17, 18, 19, 20, 21, 22, 23, 24, 25, 26, 27, 28, 29, 30, 35, 40, 50, 55, 60, 65, 70, 75, 80, 85, 90, 100, 110, 120, 140, 150, 175, or 200 nucleotide bases. In general, useful probe lengths will range from about 8 to about 200 nucleotide bases; from about 12 to about 175 nucleotide bases; from about 15 to about 150 nucleotide bases; from about 15 to about 100 nucleotide bases from about 15 to about 75 nucleotide bases; from about 15 to about 60 nucleotide bases; from about 20 to about 100 nucleotide bases; from about 20 to about 75 nucleotide bases; from about 20 to about 60 nucleotide bases; from about 20 to about 50 nucleotide bases in length. In some embodiments the probe set can comprise probes directed to at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 60, 70, 80, 90, 100, 125, 150, 175, 200, 225, 250, 275, 300, 325, 350, 375, 400, 425, 450, 475, 500, 525, 550, 575 or more, or all, of the colorectal neoplasm biomarker genes in FIG. 6 (Panel A) and FIG. 13 (Panel B).

The primers and probes disclosed herein can be detectably labeled. A label can be a molecular moiety or compound that can be detected or lead to a detectable response, which may be joined directly or indirectly to a nucleic acid. Direct labeling may use bonds or interactions to link label and probe, which includes covalent bonds, non-covalent interactions (hydrogen bonds, hydrophobic and ionic interactions), or chelates or coordination complexes. Indirect labeling may use a bridging moiety or linker (e.g. antibody, oligomer, or other compound), which is directly or indirectly labeled, which may amplify a signal. Labels include any detectable moiety, e.g., radionuclide, ligand such as biotin or avidin, enzyme, enzyme substrate, reactive group, chromophore (detectable dye, particle, or bead), fluorophore, or luminescent compound (bioluminescent, phosphorescent, or chemiluminescent label). Labels can be detectable in a homogeneous assay in which bound labeled probe in a mixture exhibits a detectable change compared to that of unbound labeled probe, e.g., stability or differential degradation, without requiring physical separation of bound from unbound forms.

Suitable detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.). As discussed above, coupling of the one or more ligand motifs and/or ligands to the detectable label may be direct or indirect. Detection may be in situ, in vivo, in vitro on a tissue section or in solution, etc.

In some embodiments, the methods include the use of alkaline phosphatase conjugated polynucleotide probes. When an alkaline phosphatase (AP)-conjugated polynucleotide probe is used, following sequential addition of an appropriate substrate such as fast blue or fast red substrate, AP breaks down the substrate to form a precipitate that allows in-situ detection of the specific target RNA molecule. Alkaline phosphatase may be used with a number of substrates, e.g., fast blue, fast red, or 5-Bromo-4-chloro-3-indolyl-phosphate (BCIP). See, e.g., as described generally in U.S. Pat. Nos. 5,780,277 and 7,033,758.

In some embodiments, the fluorophore-conjugates probes can be fluorescent dye conjugated label probes, or utilize other enzymatic approaches besides alkaline phosphatase for a chromogenic detection route, such as the use of horseradish peroxidase conjugated probes with substrates like 3,3'-Diaminobenzidine (DAB).

The fluorescent dyes used in the conjugated label probes may typically be divided into families, such as fluorescein and its derivatives; rhodamine and its derivatives; cyanine and its derivatives; coumarin and its derivatives; Cascade Blue™ and its derivatives; Lucifer Yellow and its derivatives; BODIPY and its derivatives; and the like. Exemplary fluorophores include indocarbocyanine (C3), indodicarbocyanine (C5), Cy3, Cy3.5, Cy5, Cy5.5, Cy7, Texas Red, Pacific Blue, Oregon Green 488, Alexa Fluor®-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine™), carboxy tetramethylrhodamine (TAMRA™), carboxy-X-rhodamine (ROX™) LIZ™, VIC™, NED™, PET™, SYBR, PicoGreen, RiboGreen, and the like. Descriptions of fluorophores and their use, can be found in, among other places, R. Haugland, Handbook of Fluorescent Probes and Research Products, 9th ed. (2002), Molecular Probes, Eugene, Oreg.; M. Schena, Microarray Analysis (2003), John Wiley & Sons, Hoboken, N.J.; Synthetic Medicinal Chemistry 2003/2004 Catalog, Berry and Associates, Ann Arbor, Mich.; G. Hermanson, Bioconjugate Techniques, Academic Press (1996); and Glen Research 2002 Catalog, Sterling, Va. Near-infrared dyes are expressly within the intended meaning of the terms fluorophore and fluorescent reporter group.

In some embodiments, levels of the eukaryotic biomarkers can be analyzed on a gene array. Microarray analysis can be performed on a customized gene array. Alternatively, or in addition, microarray analysis can be carried out using commercially-available systems according to the manufacturer's instructions and protocols. Exemplary commercial systems include Affymetrix GENECHIP® technology (Affymetrix, Santa Clara, Calif.), Agilent microarray technology, the NCOUNTER® Analysis System (NanoString® Technologies) and the BeadArray Microarray Technology (Illumina). Nucleic acids extracted from a stool sample can be hybridized to the probes on the gene array. Probe-target hybridization can be detected by chemiluminescence to determine the relative abundance of particular sequences.

In some embodiments, the probes and probe sets can be configured as a gene array. A gene array, also known as a microarray or a gene chip, is an ordered array of nucleic acids that allows parallel analysis of complex biological samples. Typically, a gene array includes probes that are attached to a solid substrate, for example a microchip, a glass slide, or a bead. The attachment generally involves a chemical coupling resulting in a covalent bond between the substrate and the probe. The number of probes in an array can vary, but each probe is fixed to a specific addressable location on the array or microchip. In some embodiments, the probes can be about 18 nucleotide bases, about 20 nucleotide bases, about 25 nucleotide bases, about 30 nucleotide bases, about 35 nucleotide bases, or about 40 nucleotide bases in length. In some embodiments, the probe set comprises probes directed to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 60, 70, 80, 90, 100, 125, 150, or more, or all, of the colorectal neoplasm biomarker genes in FIG. 6 (Panel A) and FIG. 13 (Panel B). The probe sets can be incorporated into high-density arrays comprising 5,000, 10,000, 20,000, 50,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000 or more different probes.

Methods of gene array synthesis can vary. Exemplary methods include synthesis of the probes followed by deposition onto the array surface by "spotting," in situ synthesis, using for example, photolithography, or electrochemistry on microelectrode arrays.

The levels of eukaryotic markers can be evaluated using a variety of methods. Expression levels can be determined either at the nucleic acid, for example, the RNA level or at the polypeptide level. RNA expression can encompass expression of total RNA, mRNA, tRNA, rRNA, ncRNA, smRNA, miRNA, and snoRNA. Expression at the RNA level can be measured directly or indirectly by measuring levels of cDNA corresponding to the relevant RNA. Alternatively, or in addition, polypeptides encoded by the RNA, RNA regulators of the genes encoding the relevant transcription factors, and levels of the transcription factor polypeptides can also be assayed. Methods for determining gene expression at the mRNA level include, for example, microarray analysis, serial analysis of gene expression (SAGE), RT-PCR, blotting, hybridization based on digital barcode quantification assays, multiplex RT-PCR, digital drop PCR (ddPCR), NanoDrop spectrophotometers, qRT-PCR, qPCR, UV spectroscopy, RNA sequencing, next-generation sequencing, lysate based hybridization assays utilizing branched DNA signal amplification such as the QuantiGene 2.0 Single Plex, and branched DNA analysis methods. Digital barcode quantification assays can include the BeadArray (Illumina), the xMAP systems (Luminex), the nCounter (Nanostring), the High Throughput Genomics (HTG) molecular, BioMark (Fluidigm), or the Wafergen microarray. Assays can include DASL (Illumina), RNA-Seq (Illumina), TruSeq (Illumina), SureSelect (Agilent), Bioanalyzer (Agilent) and TaqMan (ThermoFisher).

Levels of the eukaryotic biomarkers can also be analyzed by DNA sequencing. DNA sequencing can be performed by sequencing methods such as targeted sequencing, whole genome sequencing or exome sequencing. Sequencing methods can include: Sanger sequencing or high-throughput sequencing. High throughput sequencing can involve sequencing-by-synthesis, pyrosequencing, sequencing-by-ligation, real-time sequencing, nanopore sequencing, and Sanger sequencing. In some embodiments, isolated RNA can be used to generate a corresponding cDNA and the cDNA can be sequenced.

The sequencing methods described herein can be carried out in multiplex formats such that multiple different target nucleic acids are manipulated simultaneously. In some embodiments, different target nucleic acids can be treated in a common reaction vessel or on a surface of a particular substrate, enabling convenient delivery of sequencing reagents, removal of unreacted reagents and detection of incorporation events in a multiplex manner. In some embodiments where surface-bound target nucleic acids are involved, the target nucleic acids may be in an array format. In an array format, the target nucleic acids may be typically coupled to a surface in a spatially distinguishable manner. For example, the target nucleic acids may be bound by direct covalent attachment, attachment to a bead or other particle or associated with a polymerase or other molecule that is attached to the surface. The array may include a single copy of a target nucleic acid at each site (also referred to as a feature) or multiple copies having the same sequence can be present at each site or feature. Multiple copies are produced by amplification methods such as bridge amplification, PCR, or emulsion PCR.

In some embodiments, a normalization step can be used to control for nucleic acid recovery and variability between samples. In some embodiments, a defined amount of exogenous control nucleic acids can be added ("spiked in") to the extracted eukaryotic nucleic acids. The exogenous control nucleic acid can be a nucleic acid having a sequence corresponding to one or more eukaryotic sequences. Alternatively, or in addition, the exogenous control nucleic acid can have a sequence corresponding to the sequence found in another species, for example a bacterial sequence such as a *Bacillus subtilis* sequence. In some embodiments, the methods can include determining the levels of one or more housekeeping genes. In some embodiments, the methods can include normalizing the expression levels of biomarkers to the levels of the housekeeping genes.

The methods include the step of determining whether the measured expression levels of one, two, or more biomarkers in an experimental sample are different from the measured expression levels of one, two, or more biomarkers in a control. In another embodiment, the methods include the step of determining whether the proportion of expression levels of one, two, or more biomarkers in an experimental sample are different from the proportion of measured expression levels of one, two, or more biomarkers in a control. A difference in expression level or a proportion of expression levels can be an increase or a decrease.

The compositions disclosed herein are generally and variously useful for the detection, diagnosis and treatment of colorectal cancer. Methods of detection can include measuring the expression level in a stool sample of two or more colorectal neoplasm biomarkers selected from the biomarkers listed in any of FIG. 6 (Panel A) or FIG. 13 (Panel B) and comparing the measured expression level of the two or more colorectal neoplasm biomarker genes in the sample with the measured expression level of two or more colorectal neoplasm biomarker genes in a control. A difference in the measured expression level of two or more colorectal neoplasm biomarker genes in a patient's sample relative to the measured expression level of the two or more colorectal neoplasm biomarker genes in a control is an indication that the patient has colorectal cancer. In some embodiments, a difference in the measured expression level of two or more colorectal neoplasm biomarker genes in a patient's sample relative to the measured expression level of the two or more colorectal neoplasm biomarker genes in a control is an indication that the patient has a precancerous lesion and/or is at risk for colorectal cancer. These methods can further include the step of identifying a subject (e.g., a patient and, more specifically, a human patient) who has a colorectal neoplasm, for example, colorectal cancer or a precancerous lesion, or who is at risk for developing a colorectal neoplasm.

A colorectal neoplasm can include any form of colorectal cancer. A colorectal neoplasm can also include a polyp, for example a precancerous lesion. Colorectal cancer typically begins as a growth, termed a polyp, in the luminal lining of the colon or rectum. Colorectal polyps are generally divided into two categories: adenomatous polyps, also called adenomas; and hyperplastic and inflammatory polyps. Adenomatous polyps can give rise to colorectal cancer. The most common form of colorectal cancer, adenocarcinoma, originates in the intestinal gland cells that line the inside of the colon and/or rectum. Adenocarcinomas can include tubular adenocarcinomas, which are glandular cancers on a pedunculated stalk, and villous adenocarcinomas, which are glandular cancers that lie flat on the surface of the colon. Other colorectal cancers are distinguished by their tissue of origin. These include gastrointestinal stromal tumors (GIST), which arise from the interstitial cells of Cajal; primary colorectal lymphomas, which arise from hematologic cells; leiomyosarcomas, which are sarcomas arising from connective tissue or smooth muscle; melanomas, which arise from melanocytes: squamous cell carcinomas which arise from stratified squamous epithelial tissue and are confined to the rectum; and mucinous carcinomas, which are epithelial cancers generally associated with poor prognosis.

Symptoms of colorectal cancer can include, but are not limited to, a change in bowel habits, including diarrhea or constipation or a change in the consistency of the stool lasting longer than four weeks, rectal bleeding or blood in the stool, persistent abdominal discomfort such as cramps, gas or pain, a feeling that the bowel does not empty completely, weakness or fatigue, and unexplained weight loss. Patients suspected of having colorectal cancer may receive peripheral blood tests, including a complete blood count (CBC), a fecal occult blood test (FOBT), a liver function analysis, a fecal immunochemical test (FIT), and/or other analysis of certain tumor markers, for example carcinoembryonic antigen (CEA) and CA19-9. Colorectal cancer is often diagnosed based on colonoscopy. During colonoscopy, any polyps that are noted are removed, biopsied and analyzed to determine whether the polyp contains colorectal cancer cells or cells that have undergone a precancerous change. Each one of the specific cancers listed above can look different when viewed through an endoscope. Villous adenomas melanomas, and squamous cell carcinomas are typically flat or sessile, whereas tubular adenomas, lymphomas, leiomyosarcomas and GIST tumors are typically pedunculated. However, flat and sessile adenomas can be missed by gastroenterologists during colonoscopies. Biopsy samples can be subjected to further analysis based on genetic changes of particular genes or microsatellite instability.

Other diagnostic methods can include, sigmoidoscopy, imaging tests, for example, computed tomography (CT or CAT) scans; ultrasound, for example abdominal, endorectal or intraoperative ultrasound, magnetic resonance imaging (MRI) scans, for example endorectal MRI. Other tests such as angiography and chest x-rays can be carried out to determine whether a colorectal cancer has metastasized.

A variety of methods for staging colorectal cancer have been developed. The most commonly used system, the TNM system is based on three factors: 1) the distance that the primary tumor (T) has grown into the wall of the intestine and nearby areas; 2) whether the tumor has spread to nearby regional lymph nodes (N); 3) whether the cancer has metastasized to other organs (M). Other methods of staging include Dukes staging and the Astler-Coller classification.

The TNM system provides a four-stage classification of colorectal cancer. In Stage 1 (T1) colorectal cancer, the tumor has grown into the layers of the colon wall, but has not spread outside the colon wall or into lymph nodes. If the cancer is part of a tubular adenoma polyp, then simple excision is performed and the patient can continue to receive routine testing for future cancer development. If the cancer is high grade or part of a flat/sessile polyp, more surgery might be required and larger margins will be taken; this might include partial colectomy where a section of the colon is resected. In Stage 2 (T2) colorectal cancer, the tumor has grown into the wall of the colon and potentially into nearby tissue but has not spread to nearby lymph nodes. Surgical removal of the tumor and a partial colectomy is generally performed. Adjunct therapy, for example, chemotherapy with agents such as 5-fluorouracil, leucovorin, or capecitabine, may be administered. Such tumors are unlikely to recur, but increased screening of the patient is generally needed. In Stage 3 (T3) colorectal cancer, the tumor has spread to nearby lymph nodes, but not to other parts of the body. Surgery to remove the section of the colon and all affected lymph nodes will be required. Chemotherapy, with agents such as 5-fluorouracil, leucovorin, oxaliplatin, or capecitabine combined with oxaliplatin is typically recommended. Radiation therapy may also be used depending on the age of the patient and aggressive nature of the tumor. In Stage 4 (T4) colorectal cancer, the tumor has spread from the colon to distant organs through the blood. Colorectal cancer most frequently metastasizes to the liver, lungs and/or peritoneum. Surgery is unlikely to cure these cancers and chemotherapy and or radiation are generally needed to improve survival rates.

The methods disclosed herein are generally useful for diagnosis and treatment of colorectal cancer. The level of two or more colorectal neoplasm biomarker genes is measured in a biological sample, that is a sample from a subject. The subject can be a patient having one or more of the symptoms described above that would indicate the patient is at risk for colorectal cancer. The subject can also be a patient having no symptoms, but who may be at risk for colorectal cancer based on age (for example, above age 50), family history, obesity, diet, alcohol consumption, tobacco use, previous diagnosis of colorectal polyps, race and ethnic background, inflammatory bowel disease, and genetic syndromes, such as familial adenomatous polyposis, Gardner syndrome, Lynch syndrome, Turcot syndrome, Peutz-Jeghers syndrome, and MUTYH-associated polyposis, associated with higher risk of colorectal cancer. The methods disclosed herein are also useful for monitoring a patient who has previously been diagnosed and treated for colorectal cancer in order to monitor remission and detect cancer recurrence.

In some embodiments, the disease-state of a subject, that is, a human or non-human animal patient, is determined by pathological evaluation. For example, in one type of disease, such as colorectal cancer, the extent of disease is classified as stage 1 (T1), stage 2 (T2), stage 3 (T3), and stage 4 (T4). The colorectal cancer can be a tubular adenocarcinoma, a villous adenocarcinoma, a gastrointestinal stromal tumor, a primary colorectal lymphoma, a leiomyosarcoma, melanoma, a squamous cell carcinoma, or a mucinous carcinoma. In another type of disease, such as inflammatory bowel disease, the disease-state is determined by location of the disease along the intestinal tract and histological features such as granulomas, leukocyte infiltrates and/or crypt abscesses. Other methods for determining disease-state such as physician determination, physical symptoms, fecal occult blood test, a fecal immunochemical test, sigmoidoscopy, FIT-DNA, CT Colonography, or a colonoscopy can also be used in conjunction with the methods disclosed herein.

Also provided are methods of determining whether a subject is at risk for intestinal disease. Intestinal disease can include intestinal cancer, colorectal cancer, adenomatous polyps indicative of pre-cancerous change, irritable bowel syndrome, ulcerative colitis, Crohn's disease or other intestinal disease. The method of determining whether a subject is at risk for intestinal disease can be determined by using the invention to detect a) a sequence of deoxyribonucleic acid (DNA), b) a sequence of ribonucleic acid (RNA), c) a predicted amino acid sequence, which comprises the backbone of protein, d) expression levels of ribonucleic acid biomarkers, e) prediction in the variation of a sequence in amino acid or f) any combination of the above, wherein a difference between the control and the experimental sample can indicate that the subject is at risk for intestinal disease.

The methods and compositions are also useful for selecting a clinical plan for a subject suffering from intestinal disease. Through this method, the clinical plan can include administration of further diagnostic procedures. In some embodiments, the clinical plan can include a method of treatment.

The level of two or more colorectal neoplasm biomarker genes selected from FIG. 6 (Panel A) or FIG. 13 (Panel B) can be analyzed in a subject at risk for or having colorectal cancer. In some embodiments, the level of one, two, or more colorectal neoplasm biomarker genes selected from FIG. 6 (Panel A) or FIG. 13 (Panel B) can be analyzed in a subject at risk for or having colorectal cancer. The colorectal neoplasm biomarker genes listed in FIG. 6 (Panel A) or FIG. 13 (Panel B) can form a panel. In some embodiments, the two or more biomarkers can include combinations of 2, 3, 4, 5, 6, 7, 8, 9, 10, 11, 12, 13, 14, 15, 16, 17, 18, 19, 20, 21, 22, 23, 24, 25, 30, 35, 40, 45, 50, 60, 70, 80, 90, 100, 120, 140, 160, 180 or more of the markers in FIG. 6 (Panel A) or FIG. 13 (Panel B). In some embodiments, the markers can be contained within differentially expressed transcript clusters and/or common pathways associated with colorectal cancer. Exemplary pathways include microsatellite instability (MSI), chromosomal instability (CIN), and CpG island methylator phenotype (CIMP). In some embodiments, the pathways can be cellular components pathways, cellular response to stress, stress, and RNA binding pathways.

Algorithms for determining diagnosis, status, or response to treatment, for example, can be determined for particular clinical conditions. The algorithms used in the methods provided herein can be mathematic functions incorporating multiple parameters that can be quantified using, without limitation, medical devices, clinical evaluation scores, or biological/chemical/physical tests of biological samples. Each mathematic function can be a weight-adjusted expression of the levels (e.g., measured levels) of parameters determined to be relevant to a selected clinical condition. Because of the techniques involved in weighting and assessing multiple marker panels, computers with reasonable computational power can be used to analyze the data.

Thus, the method of diagnosis can include obtaining a stool sample from a patient at risk for or suspected of having colorectal cancer; determining the expression of two or more colorectal neoplasm biomarker genes selected from FIG. 6 (Panel A) or FIG. 13 (Panel B) and providing a test value by the machine learning algorithms that incorporate a plurality of colorectal neoplasm biomarker genes selected from any of the panels of colorectal neoplasm biomarker genes with a predefined coefficient. Exemplary machine learning algorithms include Support Vector Machine, Gradient Boosting, Adaptive Boosting, Random Forest, Naive Bayes, Decision Tree, and k-Nearest Neighbors. A significant change in expression of a plurality of colorectal neoplasm biomarker genes relative to the control, for example, a population of healthy individuals, indicates an increased likelihood that the patient has colorectal cancer and/or a precancerous lesion. In some embodiments, the expression levels measured in a sample are used to derive or calculate a probability or a confidence score. This value may be derived from expression levels. Alternatively, or in addition, the value can be derived from a combination of the expression value with other factors, for example, the patient's medical history, age, and genetic background. In some embodiments, the method can further comprise the step of communicating the test value to the patient.

Standard computing devices and systems can be used and implemented, e.g., suitably programmed, to perform the methods described herein, e.g., to perform the calculations needed to determine the values described herein. Computing devices include various forms of digital computers, such as laptops, desktops, mobile devices, workstations, personal digital assistants, servers, blade servers, mainframes, and other appropriate computers. In some embodiments, the computing device is a mobile device, such as personal digital assistant, cellular telephone, smartphone, tablet, or other similar computing device.

In some embodiments, a computer can be used to communicate information, for example, to a healthcare professional. Information can be communicated to a professional by making that information electronically available (e.g., in a secure manner). For example, information can be placed on a computer database such that a health-care professional can access the information. In addition, information can be communicated to a hospital, clinic, or research facility serving as an agent for the professional. Information transferred over open networks (e.g., the internet or e-mail) can be encrypted. Patient's gene expression data and analysis can be stored in the cloud with encryption. The method 256-bit AES with tamper protection can be used for disk encryption; SSL protocol preferably can ensure protection in data transit, and key management technique SHA2-HMAC can allow authenticated access to the data. Other secure data storage means can also be used.

The results of such analysis above can be the basis of follow-up and treatment by the attending clinician. If the expression level of two or more colorectal neoplasm biomarker genes selected from FIG. 6 (Panel A) or FIG. 13 (Panel B) is not significantly different from the expression level of the same two or more colorectal neoplasm biomarkers in a control, the clinician may determine that the patient is presently not at risk for colorectal cancer or a precancerous lesion. Such patients can be encouraged to return in the future for rescreening. The methods disclosed herein can be used to monitor any changes in the levels of the colorectal neoplasm markers over time. A subject can be monitored for any length of time following the initial screening and/or diagnosis. For example, a subject can be monitored for at least 2, 4, 6, 8, 10, 12, 14, 16, 18, 20, 25, 30, 35, 40, 45, 50, 55, or 60 months or more or for at least 1, 2, 3, 4, 5, 6, 7, 8, 9, 10, 11, 12, 13, 14, 15, 16, 17, 18, 19, 20 or more years.

The methods and compositions disclosed herein are useful for selecting a clinical plan for a subject at risk for or suffering from colorectal neoplasm. The clinical plan can include administration of further diagnostic procedures, for example, a fecal occult blood test, a fecal immunochemical test, or a colonoscopy to remove polyps or precancerous lesions. In some embodiments, the clinical plan can include a method of treatment. In some embodiments, the methods include methods of selecting a treatment for a subject having colorectal cancer. If the expression level of two or more colorectal neoplasm biomarker genes selected from FIG. 6 (Panel A) or FIG. 13 (Panel B) is significantly different from the expression level of the same two or more colorectal neoplasm biomarker genes in a control, the patient may have colorectal cancer. In these instances, further screening may be recommended, for example, increased frequency of screening using the methods disclosed herein, as well as a fetal occult blood test, a fecal immunochemical test, and/or a colonoscopy. In some embodiments, treatment may be recommended, including, for example, a colonoscopy with removal of polyps, chemotherapy, or surgery, such as bowel resection. Thus, the methods can be used to determine the level of expression of two or more colorectal neoplasm biomarker genes and then to determine a course of treatment. A subject, that is a patient, is effectively treated whenever a clinically beneficial result ensues. This may mean, for example, a complete resolution of the symptoms of a disease, a decrease in the severity of the symptoms of the disease, or a slowing of the disease's progression. These methods can further include the steps of a) identifying a subject (e.g., a patient and, more specifically, a human patient) who has colorectal cancer; and b) providing to the subject an anticancer treatment, for example, a therapeutic agent, surgery, or radiation therapy. An amount of a therapeutic agent provided to the subject that results in a complete resolution of the symptoms of a disease, a decrease in the severity of the symptoms of the disease, or a slowing of the disease's progression is considered a therapeutically effective amount. The present methods may also include a monitoring step to help optimize dosing and scheduling as well as predict outcome. Monitoring can also be used to detect the onset of drug resistance, to rapidly distinguish responsive patients from nonresponsive patients or to assess recurrence of a cancer. Where there are signs of resistance or nonresponsiveness, a clinician can choose an alternative or adjunctive agent before the tumor develops additional escape mechanisms.

The methods disclosed herein can also be used in combination with conventional methods for diagnosis and treatment of colorectal cancer. Thus, the diagnostic methods can be used along with standard diagnostic methods for colorectal cancer. For example, the methods can be used in combination with a fecal occult blood test, a fecal immunochemical test, or a colonoscopy. The methods can also be used with other colorectal cancer markers, for example, KRAS, NRAS, BRAF, CEA, CA 19-9, p53, MSL, DCC and MMR.

The diagnostic methods disclosed herein can also be used in combination with colorectal cancer treatments. Colorectal cancer treatment methods fall into several general categories: surgery, chemotherapy, radiation therapy, targeted therapy and immunotherapy. Surgery can include colectomy, colostomy along with partial hepatectomy, or protectomy. Chemotherapy can be systemic chemotherapy or regional chemotherapy in which the chemotherapeutic agents are placed in direct proximity to an affected organ. Exemplary chemotherapeutic agents can include 5-fluorouracil, oxaliplatin or derivatives thereof, irinotecan or a derivative thereof, leucovorin, or capecitabine, mitomycin C, cisplatin and doxorubicin. Radiation therapy can be external radiation therapy, using a machine to direct radiation toward the cancer or internal radiation therapy in which a radioactive substance is placed directly into or near the colorectal cancer. Targeted agents can include anti-angiogenic agents such as bevacizumab) or EGFR inhibitor monoclonal antibody (cetuximab, panitumumab), ramuciramab (anti-VEGFR2), aflibercept, regorafenib, trifluridine-tipiracil or a combination thereof. Targeted agents can also be combined with standard chemotherapeutic agents. Immunotherapy can include administration of specific antibodies, for example anti-PD-1 antibodies, anti-PD-L-1 antibodies, and time-CTLA-4 antibodies, anti-CD 27 antibodies; cancer vaccines, adoptive cell therapy, oncolytic virus therapies, adjuvant immunotherapies, and cytokine-based therapies. Other treatment methods include stem cell transplantation, hyperthermia, photodynamic therapy, blood product donation and transfusion, or laser treatment.

We may use the terms "increased", "increase" or "up-regulated" to generally mean an increase in the level of a biomarker by a statistically significant amount. In some embodiments, an increase can be an increase of at least 10% as compared to a control, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a control, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold increase, or any increase between 1.0-fold and 10-fold or greater as compared to a control.

We may use the terms "decrease", "decreased", "reduced", "reduction" or "down-regulated" to refer to a decrease in the level of a eukaryotic biomarker by a statistically significant amount. In some embodiments, a decrease can be a decrease of at least 10% as compared to a control, for example a decrease of at least about 20%, or at least about 30%, or at least about 40%, or at least about 50%, or at least about 60%, or at least about 70%, or at least about 80%, or at least about 90% or up to and including a 100% decrease (i.e. absent level as compared to a control), or any decrease between 10-100% as compared to a control, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold decrease, or any decrease between 1.0-fold and 10-fold or greater as compared to a control.

The statistical significance of an increase in a eukaryotic biomarker or a decrease in a eukaryotic biomarker can be expressed as a p-value. Depending upon the specific eukaryotic biomarker, p-value can be less than 0.05, less than 0.01, less than 0.005, less than 0.002, less than 0.001, or less than 0.0005.

A control can be a biological sample obtained from a patient or a group of patients. In some embodiments, the control can be a reference value. A control can be obtained from an individual, or a population of individuals, who have been diagnosed as healthy. Healthy individuals can include, for example, individuals who have tested negative in a fecal parasitic test, a fecal bacteria test, or an endoscopy within the last year. A control can be obtained from an individual, or a population of individuals, who have been diagnosed as diseased. Diseased individuals can include, for example, individuals who have tested positive in a fecal parasitic test, a fecal bacterial test, or an endoscopy within the last year. A control can be obtained from an individual, or a population of individuals, who had previously been diagnosed with disease but are currently in remission or are not currently suffering from the disease. A control can be obtained from an individual at one, two, or more points in time. For example, a control can be a biological sample obtained from a subject at an earlier point in time. A control can be a standard reference value for a particular biomarker. A standard reference value can be derived based on evaluating individuals of similar age, sex, gender, body size, breed, ethnic background, or general health.

An experimental sample can be a biological sample obtained from a subject. An experimental sample can be obtained from a subject with known or unknown health status. In some embodiments, health status of a subject can be determined, for example, by analysis of an experimental sample, biopsy, physical examination, laboratory findings, visual inspection or genetic analysis. The health status of a subject that can be determined via an experimental sample can be diseased, at risk for disease, or healthy.

Articles of Manufacture

Also provided are kits for detecting and quantifying selected colorectal neoplasm biomarkers in a biological sample, for example, a stool sample. Accordingly, packaged products (e.g., sterile containers containing one or more of the compositions described herein and packaged for storage, shipment, or sale at concentrated or ready-to-use concentrations) and kits, are also within the scope of the invention. A product can include a container (e.g., a vial, jar, bottle, bag, microplate, microchip, or beads) containing one or more compositions of the invention. In addition, an article of manufacture further may include, for example, packaging materials, instructions for use, syringes, delivery devices, buffers or other control reagents.

The kit can include a compound or agent capable of detecting RNA corresponding to two or more of the colorectal neoplasm biomarker genes selected from FIG. 6 (Panel A) or FIG. 13 (Panel B) in a biological sample; and a standard; and optionally one or more reagents necessary for performing detection, quantification, or amplification. In some embodiments, the kit can include a compound or agent capable of detecting RNA corresponding to two or more of a B cell marker, a T cell marker, or an immunoglobulin, in a biological sample; and a standard; and optionally one or more reagents necessary for performing detection, quantification, or amplification. The compounds, agents, and/or reagents can be packaged in a suitable container. The kit can further comprise instructions for using the kit to detect and quantify nucleic acid. For example, the kit can include: (1) a probe, e.g., an oligonucleotide, e.g., a detectably labeled oligonucleotide, which hybridizes to a nucleic acid sequence corresponding to a two or more of the colorectal biomarker genes selected from selected from FIG. 6 (Panel A) or FIG. 13 (Panel B) or a B cell marker, a T cell marker, or an immunoglobulin or (2) a pair of primers useful for amplifying a nucleic acid molecule corresponding to two or more of the colorectal biomarker genes selected from selected from FIG. 6 (Panel A) or FIG. 13 (Panel B) or a B cell marker, a T cell marker, or an immunoglobulin. The kit can further include probes and primers useful for amplifying one or more housekeeping genes. The kit can also include a buffering agent, a preservative, and/or a nucleic acid or protein stabilizing agent. The kit can also include components necessary for detecting the detectable agent (e.g., an enzyme or a substrate). The kit can also contain a control or a series of controls which can be assayed and compared to the test sample contained. Each component of the kit can be enclosed within an individual container and all of the various containers can be within a single package, along with instructions for interpreting the results of the assays performed using the kit. In some embodiments, the kits can include primers or oligonucleotide probes specific for one or more control markers. In some embodiments, the kits include reagents specific for the quantification of two or more of the colorectal biomarkers selected from selected from FIG. 6 (Panel A) or FIG. 13 (Panel B) or a B cell marker, a T cell marker, or an immunoglobulin.

In some embodiments, the kit can include reagents specific for the separation of human cells from bacterial cells and other stool components and extraction of human mRNA from a patient's stool sample. Thus, the kit can include buffers, emulsion beads, silica beads, stabilization reagents and various filters and containers for centrifugation. The kit can also include instructions for stool handling to minimize contamination of samples and to ensure stability of human mRNA in the stool sample. The kit can also include items to ensure sample preservation, for example, coolants or heat packs. In some embodiments, the kit can include a stool collection device.

The product may also include a legend (e.g., a printed label or insert or other medium describing the product's use (e.g., an audio- or videotape or computer readable medium)). The legend can be associated with the container (e.g., affixed to the container) and can describe the manner in which the reagents can be used. The reagents can be ready for use (e.g., present in appropriate units), and may include one or more additional adjuvants, carriers or other diluents. Alternatively, the reagents can be provided in a concentrated form with a diluent and instructions for dilution.

EXAMPLES

Example 1: Human Stool Sample Procurement

Human Stool Collection: Patients were asked to defecate into a bucket that fit over a toilet seat and the resulting samples were stored in a freezer until they were transported to the Kharkiv National Medical University (Kharkiv, Ukraine). The stool was aliquoted into 50 mL conical tubes and stored at −80° C. The samples were shipped from Kharkiv National Medical University on dry ice to Capital Biosciences (Gaithersburg, Md.) and immediately transferred to a −80° C. freezer. From there, the samples were shipped on dry ice to BioGenerator Labs (Saint Louis, Mo.) where they were stored in a −80° C. freezer until extraction.

Human Sample Types: Stool samples were obtained from 195 patients with colorectal cancer (stage I-IV), 126 patients with pre-cancerous adenomas, 125 patients had negative findings on a colonoscopy, and 8 patients had benign polyps. resulting in 454 aggregate samples. Healthy individuals were patients with no history of colorectal cancer, inflammatory bowel disease, celiac disease, irritable bowel syndrome, diarrhea within the last 20 days or any other gastrointestinal disease. Diseased individuals were patients diagnosed with colorectal cancer and precancerous polyps. Colorectal cancer patients had been diagnosed with stage I-stage IV colorectal cancer via colonoscopy and subsequent biopsy within the last month and had not yet received any post-biopsy treatment, which can include chemotherapy, radiation, and/or surgery. Polyp patients provided a stool sample prior to undergoing a colonoscopy where the physician detected a polyp that was deemed to be precancerous via a subsequent biopsy and histological evaluation. The healthy individuals were matched with polyp and cancer patients based on gender and age brackets (50-60 years, 60-70 years, 70-80 years and 80-90 years). The patients used for this study were consented by Capital Biosciences. The Schulman Internal Review Board provided ethical oversight for this study.

Example 2: Human Nucleic Acid Extraction

Total Nucleic Acid Extraction: Each stool sample was placed into a 50 mL conical tube. Approximately 1,000-25,000 mg of stool were added to each tube. An additional 20-40 mL of solution were added to each tube. This solution contained a mixture of Hanks Balanced Salt Solution (HBSS) (Sigma-Aldrich) with 0.05% Tween-20 (Sigma-Aldrich) and 0.0002% RNAse Inhibitor (Sigma-Aldrich). The stool was suspended into solution and rotated at approximately 0-10° C. for 0-10 minutes. The solution was centrifuged at 1000 rpm at 4° C. for 10 minutes and the supernatant was discarded. Approximately 4-10 mL of Easy-Mag® Lysis Buffer (bioMerieux) was added to the pellet and the pellet was re-suspended into solution. The solution was centrifuged at 2500-3500 rpm at 20-25° C. for 10-15 minutes. During the differential centrifugation, the solution separated into three layers. The bottom layer included solid cellular debris, the middle layer was a hydrophilic layer enriched for human nucleic acid and the top layer was a hydrophobic lipid layer. The top two layers were transferred to a new 15 mL conical tube and the solution was again centrifuged at 2500 rpm at 20-25° C. for 10 minutes. The result from this centrifugation step was separation into three layers: the bottom layer was solid cellular debris, the middle layer was a hydrophilic layer enriched for human nucleic acid and the top layer was a hydrophobic lipid layer. To screen large debris from the solution, a 20 uL pipette tip was placed onto a 1 mL pipette tip and 2 mL of the hydrophilic layer was pipetted from the 15 mL tube and transferred to an EasyMag® Disposable cartridge (bioMerieux). Additionally, 60 uL of EasyMag® Magnetic Silica (bioMerieux) was added to the cartridge. The beads were mixed into the solution for 0.5-1 minute using a pipette. The nucleic acids, which were bound to the beads, were eluted into a buffer solution using the Specific A Protocol according to the manufacturer's directions. The volume of the eluted nucleic acids was 70 uL. This nucleic acid solution was pipetted into a 1.5 mL tube and placed on ice. The same EasyMag® Disposable cartridges (bioMerieux) that were used in the previous step were then reloaded with an additional 2 mL of the hydrophilic layer from the same solution in the 15 mL tube used previously using the same technique to screen out large debris. An additional 20 uL of EasyMag® Magnetic Silica (bioMerieux) was added to the cartridge. The beads were mixed into the solution for 0.5-1 minute using a pipette. As described above, the nucleic acids, which were bound to the beads, were eluted into a buffer solution using the Specific A Protocol according to the manufacturer's directions. The volume of the eluted nucleic acids was 70 uL. This nucleic acid solution was pipetted into the original 1.5 mL tube that already contained first 70 uL eluate and the combined solution was placed on ice.

DNAse Treatment: The 140 uL solution was treated with Baseline-Zero-DNase (Epicenter) at 35-40° C. for 20-40 minutes. A 1-2 mL aliquot of EasyMag® Lysis Buffer was added to the DNAse treated solution and the sample was transferred to a new EasyMag® Disposable cartridge. The entire solution was added to the new cartridge along with 60 uL of EasyMag® Magnetic Silica. The nucleic acids, which were bound to the beads, were eluted into a buffer solution using the EasyMag® Generic Protocol according to the manufacturer's directions. The volume of the eluted nucleic acids was 25 uL. This nucleic acid solution was pipetted into a 1.5 mL tube and stored at 0-6° C.

Example 3: Measurement of Human Nucleic Acid Levels in Human Stool Samples

Extraction Results: Using the sample that was extracted above, 1 uL was evaluated for total nucleic acid and RNA integrity using the Agilent 2100 Bioanalyzer. The samples were analyzed qualitatively and quantitatively. Electrophoretic analysis was used to check the quality of the extracted RNA. The results of the Bioanalyzer output were analyzed by gel electrophoresis as shown in FIG. 1 and FIG. 2. The electrophoresis file (FIG. 1) was read by comparing the bands for each sample to the bands represented by the size markers in the RNA ladder (shown in the first lane of the electropherogram) and identifying the 18S and 28S ribosomal RNA bands. The ribosomal RNA (rRNA) are the two large and prominent bands around the 2,000 nucleotide marker on the standardization ladder. Qualitatively, adequate banding and darker band intensities indicated that ample intact nucleic acid was available for further analysis such as microarray sequencing, polymerase chain reaction (PCR), nucleic acid sequencing, molecular barcoding, or probe-capture. FIG. 2 shows an example of an electropherogram. The electropherogram is a graphical representation for each electrophoresis with a quantification of the total RNA mass, RIN, and total rRNA mass. The gel electrophoresis analysis provided information on the total nucleic acid and the RNA integrity. Electrophoresis diagrams and electropherograms were analyzed for each sample to determine if the sample was eligible for downstream analysis. In one example, 120 sample that were extracted using the methods described in the invention were analyzed for RNA quality such that of the 120 samples analyzed, 110 passed quality check in terms of RNA Integrity and RNA mass (FIG. 3).

The electropherograms and electrophoresis traces were used to compare samples passing quality check using the RNA extraction methods described in the invention compared to the RNA extraction methods described in the literature. In comparison to the protocol described in the literature, the nucleic acid extraction method described above increased the average RIN to 4.88 (n=168). Additionally, the total time required to complete the protocol was decreased from 3 days to 5 hours. The total RNA extraction method significantly increased the number of samples eligible for transcriptome analysis from 50%, as described in the literature, to 98.2% in the described protocol (n=168; p<0.0001) as measured by ribosomal RNA integrity and mass (FIG. 4).

Example 4: Analysis of RNA Transcripts

Of the 454 samples that were subjected to total RNA extraction, 399 of these samples were eligible for transcriptome analysis based on direct visualization of the ribosomal RNA bands using an Agilent Bioanalyzer. Subsequently, 342 samples were randomly selected from the 399 available samples to undergo whole-transcriptome analysis using the Affymetrix GeneChip™ Human Transcriptome Array 2.0 (Santa Clara, Calif.). Of these 342 samples, 4 samples failed amplification and 8 patients with polyps were determined to have hyperplastic benign polyps through a subsequent biopsy. These 12 samples were removed from the analysis, resulting in 330 samples for final analysis.

Approximately 100 ng of DNase-free fecal RNA was amplified with the Ambio WT-pico kit with subsequent hybridization to the Affymetrix GeneChip™ Human Transcriptome Array 2.0 as per the manufacturer's protocol. All samples were normalized using the Signal Space Transformation-Robust Multiarray Analysis (SST-RMA) with the Affymetrix Expression Console™.

Of the 70,523 transcript clusters in the Affymetrix Microarray, a subset of 5,149 transcript clusters that correspond to 3,977 genes were preselected to evaluate for differential expression. This initial selection reduced the false discovery rate and filtered out genes that have no known function in cancer development and progression. We explored seven machine learning classifiers (Support Vector Machine, Gradient Boosting, Adaptive Boosting, Random Forest, Naive Bayes, Decision Tree, and k-Nearest Neighbors) for colorectal neoplasm detection.

The 330 individuals were split into a training set of 265 individuals and a testing set of 65 individuals. The training set was used to identify the differentially expressed genes and build a computational model, whereas the testing set was used to determine the detection accuracy of the computational model. The standard LIMMA package was used to identify a subset of RNA transcript clusters which were differentially expressed between individuals with either precancerous adenomas or CRC and individuals with no findings on a colonoscopy. All biomarkers were ranked according to the log odds scores and the 200 highest ranked biomarkers (p<0.05) served as the features in building the machine learning model (FIG. 4). A heat map describing the hierarchical clustering of these genes is summarized in FIG. 5A and significant pathways associated with the differentially expressed genes are summarized in FIG. 5B. There were five gene clusters associated with the differentially expressed transcripts within the three populations to segregate individuals with colorectal neoplasm from healthy individuals. The differentially expressed pathways showed enrichment for 22 Common GeneGO Canonical Pathways where the vast majority (77.7%) were upregulation of the Cellular Components pathway. Most notable was the upregulation of cellular response to stress, response to stress, and RNA binding. Common pathways associated with the disease were identified by analyzing the top 200 differentially expressed transcript clusters with GAGE software. The pathways associated with the disease are shown in FIG. 5B. The Support Vector Machine Model (v-SVM) with RBF kernel was chosen for model development. The kernel function allows for the calculation of the distance between individuals by expanding the features into a higher dimensional space which is not explicitly computed. SVM finds the maximum margin hyperplane that separates the label groups. The parameter v defines the lower bound of the fraction of individuals that are used to determine the maximum margin. The SVM model was trained using expression levels for the 200 transcripts from all 265 individuals in the training set. This multi-target RNA biomarker algorithm was used on the 65 individuals within the testing set and detected 79% (34 out of 43) of all individuals that had positive findings on a screening colonoscopy. The algorithm correctly predicted 95% of individuals with precancerous adenomas ranging in size from 5 mm to 12 mm, 57% of individuals with Stage I colorectal cancer, 75% of individuals with Stage II colorectal cancer, 66% of individuals with Stage II colorectal cancer, and 83% of individuals with Stage IV colorectal cancer. The model's sensitivity for colorectal cancer was directly correlated with size such that 60% of tumors ≤3.5 cm were accurately detected whereas 83% of tumors ≥5.0 cm in size were accurately detected. The model attained a specificity of 59% whereby 13 of the 22 individuals with negative findings on a colonoscopy were correctly identified by the model. Overall, the model attained a sensitivity for colorectal neoplasms of 79%, a sensitivity for precancerous adenomas of 95% and a specificity of 59%.

Technological and biological replicates showed a high concordance for luminescence levels for all genes (FIG. 10). Perfect technical replicates, whereby the RNA was isolated and evaluated on the same day, showed the highest level of concordances ($R^2$>0.990) (FIG. 10A). Technological replicates that were separated by time also showed a high level of concordance ($R^2$>0.989). These replicates were derived by extracting RNA for both replicates on the same day, however one replicate was analyzed on day 0 and a second replicate was analyzed 6 months later (FIG. 10B). Finally, biological replicates also showed a high level of concordances ($R^2$>0.986). These biological replicates were developed by taking samples from different segments of a stool that was derived from the same individual (FIG. 10C). The RNA was extracted separately and analyzed on different days.

When analyzing only 5,149 genes that have been implicated in colorectal cancer development or progression, a subset of the whole transcriptome, adjusted R-squared values improved for all three cohorts of replicates. These replicates showed comparable levels of concordance as described above (FIG. 11A-C).

Example 5: Animal Stool Sample Procurement

Stool Collection: Samples were collected locally in St. Louis, Mo. by cat and dog owners. Once cats defecated into a litter box, feline owners were asked to transfer the sample into a 50 mL conical tube and store the tube at −20° C. Once dogs defecated outdoors, canine owners were asked to transfer the sample into a 50 mL conical tube and store the tube at −20° C. Within one week of collection, samples were collected and manually transferred to BioGenerator Labs (Saint Louis, Mo.) where they were stored in a −80° C. freezer until extraction.

Sample Types: Stool samples were all obtained from healthy animals of varying ages, breeds and genders. 4 samples were collected from 4 different cats and an additional 4 samples were collected from 4 different dogs, resulting in 8 aggregate samples. One cat had recently been diagnosed with ringworm, but all other animals were asymptomatic and had not exhibited any signs of gastrointestinal distress within the last 30 days.

Example 6: Animal Nucleic Acid Extraction

Total Nucleic Acid Extraction: Each stool sample was placed into a 50 mL conical tube. Approximately 1,000-25,000 mg of stool were added to each tube. An additional 20-40 mL of solution were added to each tube. This solution contained a mixture of Hanks Balanced Salt Solution (HBSS) (Sigma-Aldrich) with 0.05% Tween-20 (Sigma-Aldrich) and 0.0002% RNAse Inhibitor (Sigma-Aldrich). The stool was suspended into solution and rotated at approximately 0-10° C. for 0-10 minutes. The solution was centrifuged at 1000 rpm at 4° C. for 10 minutes and the supernatant was discarded. Approximately 4-10 mL of Easy-Mag® Lysis Buffer (bioMerieux) was added to the pellet and the pellet was re-suspended into solution. The solution was centrifuged at 2500-3500 rpm at 20-25° C. for 10-15 minutes. During the differential centrifugation, the solution separated into three layers. The bottom layer included solid cellular debris, the middle layer was a hydrophilic layer enriched for human nucleic acid and the top layer was a hydrophobic lipid layer. The top two layers were transferred to a new 15 mL conical tube and the solution was again centrifuged at 2500 rpm at 20-25° C. for 10 minutes. The result from this centrifugation step was separation into three layers: the bottom layer was solid cellular debris, the middle layer was a hydrophilic layer enriched for human nucleic acid and the top layer was a hydrophobic lipid layer. To screen large debris from the solution, a 20 uL pipette tip was placed onto a 1 mL pipette tip and 2 mL of the hydrophilic layer was pipetted from the 15 mL tube and transferred to an EasyMag® Disposable cartridge (bioMerieux). Additionally, 60 uL of EasyMag® Magnetic Silica (bioMerieux) was added to the cartridge. The beads were mixed into the solution for 0.5-1 minute using a pipette. The nucleic acids, which were bound to the beads, were eluted into a buffer solution using the Specific A Protocol according to the manufacturer's directions. The volume of the eluted nucleic acids was 70 uL. This nucleic acid solution was pipetted into a 1.5 mL tube and placed on ice. The same EasyMag® Disposable cartridges (bioMerieux) that were used in the previous step were then reloaded with an additional 2 mL of the hydrophilic layer from the same solution in the 15 mL tube used previously using the same technique to screen out large debris. An additional 20 uL of EasyMag® Magnetic Silica (bioMerieux) was added to the cartridge. The beads were mixed into the solution for 0.5-1 minute using a pipette. As described above, the nucleic acids, which were bound to the beads, were eluted into a buffer solution using the Specific A Protocol according to the manufacturer's directions. The volume of the eluted nucleic acids was 70 uL. This nucleic acid solution was pipetted into the original 1.5 mL tube that already contained first 70 uL eluate and the combined solution was placed on ice.

DNAse Treatment: The 140 uL solution was treated with Baseline-Zero-DNase (Epicenter) at 35-40° C. for 20-40 minutes. A 1-2 mL aliquot of EasyMag® Lysis Buffer was added to the DNAse treated solution and the sample was transferred to a new EasyMag® Disposable cartridge. The entire solution was added to the new cartridge along with 60 uL of EasyMag® Magnetic Silica. The nucleic acids, which were bound to the beads, were eluted into a buffer solution using the EasyMag® Generic Protocol according to the manufacturer's directions. The volume of the eluted nucleic acids was 25 uL. This nucleic acid solution was pipetted into a 1.5 mL tube and stored at 0-6° C.

Example 7: Measurement of Nucleic Acid Levels in Animal Stool Samples

Extraction Results: Using the samples that were extracted above, 1 uL of each was evaluated for total nucleic acid and RNA integrity using the Agilent 2100 Bioanalyzer. The samples were analyzed qualitatively and quantitatively. The results of the Bioanalyzer output were analyzed by gel electrophoresis as shown in FIG. 7. The panel in FIG. 7 shows RNA Bioanalyzer traces of 1 uL from 8 samples that were run using Agilent RNA 6000 Nano Kits. The gel electrophoresis analysis provided information on the total nucleic acid and the RNA integrity and mass. The electrophoresis file was read by comparing the bands for each sample to the bands represented by the size markers in the RNA ladder (shown in the first lane of the electropherogram) and identifying the 18S and 28S eukaryotic ribosomal RNA bands. Qualitatively, adequate banding and darker band intensities indicated that ample intact nucleic acid was available for further analysis such as microarray sequencing, polymerase chain reaction (PCR), nucleic acid sequencing, molecular barcoding, or probe-capture. The sample quality was also analyzed qualitatively using the RNA Integrity Number. FIG. 7B shows the RNA integrity value for each of the same 8 samples that were run using Agilent RNA 6000 Nano Kits. The sample mass was also analyzed quantitatively. FIG. 7C shows the estimated eukaryotic RNA concentration (ug/uL) from the same 8 samples that were run using Agilent RNA 6000 Nano Kits. The eukaryotic RNA concentration was estimated using the area under the curve of the BioAnalyzer traces. As shown in FIG. 7B-C, the average RIN for all samples was 4.2 and the average eukaryotic mass for all samples was 61.4 ng/µL. The quantitative and qualitative measurements indicated that all samples were eligible for biomarker expression analysis (n=8).

Example 8: Analysis of RNA Transcripts in Animal Stool Samples

All canine samples that were eligible for biomarker expression analysis (n=4) were evaluated using RT-qPCR. For these four canine samples, 5 primers were designed to evaluate portions of the canine genome. Two primers were designed to act as a positive control by evaluating the heavy chain of IgM on canine T-cells. Three additional primers were designed to evaluate two separate rearrangements that can occur in canine lymphoid precursors to detect T-cell specific RNA. Each RT-PCR reaction contained 10 uL 2× Master Mix (New England Biolabs), 1 uL 20× Enzyme Mix (New England BioLabs), 0.8 uL of 10 uM forward primer (Eurofins Genomics), 0.8 uL of 10 uM reverse primer (Eurofins Genomics), 1 uL 20× SYBR Green I, 2 uL RNA, and 4.4 uL molecular biology grade $H_2O$ (Thermo Scientific). The nucleic acids were amplified using an Applied Biosystems QuantStudio5 qPCR machine. The thermocycler protocol was as follows: 25 minutes at 55° C. to reverse transcribe the RNA into DNA, reverse transcriptase inactivation at 95° C. for 1 minute, 60 cycles of 10 seconds at 95° C. and 45 seconds at 60° C. for amplification and signal collection, and then a melt curve from 70° C.-95° C. Of the 4 canine samples that were subjected to total RNA extraction, 75% of the samples showed amplification of the positive control (C-mu IgM) (FIG. 8A). Of the individuals that showed amplification of the positive control, 100% (n=3) showed amplification of both T-cell specific RNA transcripts. One of the T-cell specific transcripts amplified at 35 cycles and the other T-cell specific transcript amplified at 50 cycles (FIG. 8B).

All feline samples that were eligible for biomarker expression analysis (n=5) were evaluated using RT-qPCR. For these four feline samples, two primers were designed to act as a positive control. These probes evaluated feline Actin-B to determine if there was feline RNA present in the nucleic acid extract. Each reaction contained: 10 uL 2× Master Mix (New England BioLabs), 1 uL 20× Enzyme Mix (New England BioLabs), 0.8 uL of 10 uM forward primer (Eurofins Genomics), 0.8 uL of 10 uM reverse primer (Eurofins Genomics), 1 uL 20× SYBR Green I, 2 uL RNA, and 4.4 uL molecular biology grade $H_2O$ (Thermo Scientific). The solution was amplified using an Applied Biosystems QuantStudio5 qPCR machine. The thermocycler protocol was as follows: 25 minutes at 55° C. to reverse transcribe the RNA into DNA, reverse transcriptase inactivation at 95° C. for 1 minute, 60 cycles of 10 seconds at 95° C. and then 45 seconds at 60° C. for amplification and signal collection. Of the 4 feline samples that were subjected total RNA extraction, 75% of the samples (n=4) showed amplification of the positive control (feline Actin-B) (FIG. 9).

Example 9: Analysis of Canine B-cell Transcripts

All canine samples that were eligible for biomarker expression analysis (n=4) were evaluated using RT-qPCR. For these 4 canine samples, 6 primer sets were designed to evaluate portions of the canine genome related to lymphocytes (FIG. 15A). Of the 6 primer sets designed, one primer set was used to evaluate two separate rearrangements that can occur in canine lymphoid precursors to detect B-cell specific RNA. Each reaction contained 10 uL 2× Master Mix (New England Biolabs), 1 uL 20× Enzyme Mix (New England BioLabs), 0.8 uL of 10 uM forward primer (Eurofins Genomics), 0.8 uL of 10 uM reverse primer (Eurofins Genomics), 1 uL 20× SYBR Green I, 2 uL RNA, and 4.4 uL molecular biology grade $H_2O$ (Thermo Scientific). The solution was amplified using an Applied Biosystems QuantStudio5 qPCR machine. The thermocycler protocol was as follows: 25 minutes at 55° C. to reverse transcribe the RNA into DNA, reverse transcriptase inactivation at 95° C. for 1 minute, 60 cycles of 10 seconds at 95° C. and 45 seconds at 60° C. for amplification and signal collection, and then a melt curve from 70° C.–95° C. Examples of these amplification reactions are shown in FIG. 16A. There were 2 B-cell specific RT-qPCR reactions for each sample (n=8) and of these reactions, 87.5% (7 of 8) showed amplification of B-cell related transcripts. B-cell specific transcripts amplified between cycles 30 and 35 (FIG. 16A).

Example 10: Extraction of Feline Sample Replicates

Stool Collection: Samples were collected locally in St. Louis, Mo. by cat owners. Once cats defecated into a litter box, feline owners were asked to transfer the sample into a 50 mL conical tube and store the tube at −20° C. Within one week of production, samples were collected and manually transferred to BioGenerator Labs (Saint Louis, Mo.) where they were stored in a −80° C. freezer until extraction.

Sample Types: Stool samples were all obtained from healthy animals of varying ages, breeds and genders. 8 samples were collected from 4 different cats. For some cats, up to three biological replicates were collected. We refer to a biological replicate as a stool sample from the same cat collected from separate bowel movements. One cat had recently been diagnosed with ringworm, but all other animals were asymptomatic and had not exhibited any signs of gastrointestinal distress within the last 30 days.

Total Nucleic Acid Extraction: Each stool sample was placed into a 50 mL conical tube. Approximately 1,000-25,000 mg of stool were added to each tube. An additional 20-40 mL of solution were added to each tube. This solution contained a mixture of Hanks Balanced Salt Solution (HBSS) (Sigma-Aldrich) with 0.05% Tween-20 (Sigma-Aldrich) and 0.0002% RNAse Inhibitor (Sigma-Aldrich). The stool was suspended into solution and rotated at approximately 0-10° C. for 0-10 minutes. The solution was centrifuged at 1000 rpm at 4° C. for 10 minutes and the supernatant was discarded. Approximately 4-10 mL of EasyMag® Lysis Buffer (bioMerieux) was added to the pellet and the pellet was re-suspended into solution. The solution was centrifuged at 2500-3500 rpm at 20-25° C. for 10-15 minutes. During the differential centrifugation, the solution separated into three layers. The bottom layer included solid cellular debris, the middle layer was a hydrophilic layer enriched for human nucleic acid and the top layer was a hydrophobic lipid layer. The top two layers were transferred to a new 15 mL conical tube and the solution was again centrifuged at 2500 rpm at 20-25° C. for 10 minutes. The result from this centrifugation step was separation into three layers: the bottom layer was solid cellular debris, the middle layer was a hydrophilic layer enriched for human nucleic acid and the top layer was a hydrophobic lipid layer. To screen large debris from the solution, a 20 uL pipette tip was placed onto a 1 mL pipette tip and 2 mL of the hydrophilic layer was pipetted from the 15 mL tube and transferred to an EasyMag® Disposable cartridge (bioMerieux). Additionally, 60 uL of EasyMag® Magnetic Silica (bioMerieux) was added to the cartridge. The beads were mixed into the solution for 0.5-1 minute using a pipette. The nucleic acids, which were bound to the beads, were eluted into a buffer solution using the Specific A Protocol according to the manufacturer's directions. The volume of the eluted nucleic acids was 70 uL. This nucleic acid solution was pipetted into a 1.5 mL tube and placed on ice. The same EasyMag® Disposable cartridges (bioMerieux) that were used in the previous step were then reloaded with an additional 2 mL of the hydrophilic layer from the same solution in the 15 mL tube used previously using the same technique to screen out large debris. An additional 20 uL of EasyMag® Magnetic Silica (bioMerieux) was added to the cartridge. The beads were mixed into the solution for 0.5-1 minute using a pipette. As described above, the nucleic acids, which were bound to the beads, were eluted into a buffer solution using the Specific A Protocol according to the manufacturer's directions. The volume of the eluted nucleic acids was 70 uL. This nucleic acid solution was pipetted into the original 1.5 mL tube that already contained first 70 uL eluate and the combined solution was placed on ice.

DNAse Treatment: The 140 uL solution was treated with Baseline-Zero-DNase (Epicenter) at 35-40° C. for 20-40 minutes. A 1-2 mL aliquot of EasyMag® Lysis Buffer was added to the DNAse treated solution and the sample was transferred to a new EasyMag® Disposable cartridge. The entire solution was added to the new cartridge along with 60 uL of EasyMag® Magnetic Silica. The nucleic acids, which were bound to the beads, were eluted into a buffer solution using the EasyMag® Generic Protocol according to the manufacturer's directions. The volume of the eluted nucleic acids was 25 uL. This nucleic acid solution was pipetted into a 1.5 mL tube and stored at 0-6° C.

Example 11: Measurement of Nucleic Acid Levels in Feline Sample Replicates

Extraction Results: Using the samples that were extracted above, 1 uL of each was evaluated for total nucleic acid and RNA integrity using the Agilent 2100 Bioanalyzer. The samples were analyzed qualitatively and quantitatively. The results of the Bioanalyzer output were analyzed by gel electrophoresis as shown in FIG. 14. FIG. 14 shows RNA Bioanalyzer traces of 1 uL from 8 samples that were run using Agilent RNA 6000 Nano Kits. This included 4 individual cats. The gel electrophoresis analysis provided information on the total nucleic acid and the RNA integrity and mass. The electrophoresis file was read by comparing the bands for each sample to the bands represented by the size markers in the RNA ladder (shown in the first lane of the electropherogram) and identifying the 18S and 28S eukaryotic ribosomal RNA bands. Qualitatively, adequate banding and darker band intensities indicated that ample intact nucleic acid was available for further analysis such as microarray sequencing, polymerase chain reaction (PCR), nucleic acid sequencing, molecular barcoding, or probe-capture. 100% of the samples were eligible for analysis based on RNA integrity number and amount of eukaryotic mass. The eukaryotic concentration was estimated based on the area under the 18S and 28S eukaryotic ribosomal RNA bands of the BioAnalyzer traces. FIG. 14 shows biological replicates for 4 individual cats. There was similar banding between biological replicates and distinct banding for individual cats (FIG. 14).

Example 12: Analysis of RNA Transcripts in Feline Sample Replicates

All individual feline samples that were eligible for biomarker expression analysis (n=5) were evaluated using RT-qPCR. A total of 4 primer sets were designed to evaluate lymphocyte related transcripts and epithelial cell related controls (FIG. 15B). One primer set was designed to evaluate rearrangements that can occur in feline lymphoid precursors to detect T-cell specific RNA. Each reaction contained 10 uL 2× Master Mix (New England BioLabs), 1 uL 20× Enzyme Mix (New England BioLabs), 0.8 uL of 10 uM forward primer (Eurofins Genomics), 0.8 uL of 10 uM reverse primer (Eurofins Genomics), 1 uL 20× SYBR Green I, 2 uL RNA, and 4.4 uL molecular biology grade $H_2O$ (Thermo Scientific). The solution was amplified using an Applied Biosystems QuantStudio5 qPCR machine. The thermocycler protocol was as follows: 25 minutes at 55° C. to reverse transcribe the RNA into DNA, reverse transcriptase inactivation at 95° C. for 1 minute, 60 cycles of 10 seconds at 95° C. and then 45 seconds at 60° C. for amplification and signal collection. Examples of these amplification events are shown in FIG. 16B. Of the five feline samples that were analyzed for select T-cell rearrangements, in a total of 12 reactions, 75% of the reactions showed amplification of the T-cell related transcripts. All T-cell rearrangements tested showed amplification in at least one cat (FIG. 16B).

Example 13: NanoString Analysis

To further analyze genes associated with human colorectal cancer and precancerous adenomas, an additional 70 human samples were subjected to the RNA extraction method described above. The extracted RNA was analyzed using the NanoString nCounter Analysis System, which utilizes a digital color-coded barcode technology that is based on direct multiplexed measurement of gene expression. Of the 70 samples, 48 were analyzed using the nCounter® PanCancer Pathways Panel, which includes 770 genes from 13 cancer-associated canonical pathways including: MAPK, STAT, PI3K, RAS, Cell Cycle, Apoptosis, Hedgehog, Wnt, DNA Damage Control, Transcriptional Regulation, Chromatin Modification, and TGF-β. The remaining 22 samples were analyzed using the nCounter® PanCancer Progression Panel, which includes 770 genes from each step in the cancer progression process including: angiogenesis, extracellular matrix remodeling (ECM), epithelial-to-mesenchymal transition (EMT), and metastasis. These 22 samples were also evaluated for 10 "spike-in" genes, including ACTB, B2M, BMP3, CD274, CD8A, GAPDH, HPRT1, N-BLR, NDRG4 and RNU2-1.

In addition to the list of genes identified in FIG. 6 (Panel A), the top 200 differentially expressed genes, we also analyzed additional genes that were associated with colorectal cancer and precancerous adenomas. We also analyzed all genes that were identified as highly expressed or differentially expressed on the NanoString nCounter Analysis System. This analysis included using the nCounter® PanCancer Pathways Panel, the nCounter® PanCancer Progression Panel, and the "spike-in" genes. We used this information to develop a 400 gene RNA biomarker signature for colorectal cancer and precancerous adenomas (FIG. 13 (Panel B)).

What is claimed is:

1. A method of isolating eukaryotic nucleic acid from a stool sample, the method comprising:
   a) mixing the sample with a buffer, a surfactant and a ribonuclease inhibitor to form a suspension;
   b) separating the suspension into a portion enriched for eukaryotic cells and a portion enriched for bacterial cells and retaining the portion enriched for eukaryotic cells;
   c) adding a chaotropic agent and optionally a surfactant to the portion enriched for eukaryotic cells to form a lysate;
   d) fractioning the lysate into a cell debris layer, a layer comprising eukaryotic nucleic acids and a lipid layer; and
   e) collecting the layer comprising eukaryotic nucleic acids and optionally the lipid layer.

2. The method of claim 1, further comprising providing a stool sample.

3. The method of claim 1, wherein the stool sample is a human stool sample.

4. The method of claim 1, wherein the separating step comprises centrifugation or a column-based method.

5. The method of claim 1, wherein the separating step utilizes targeted probes that bind eukaryotic cells.

6. The method of claim 1, wherein the separating step utilizes differential filtration.

7. The method of claim 1, wherein i) step a) is repeated one, two, three, four or more times, ii) step b) is repeated one, two, three, four or more times, or iii) both step a) and step b) are repeated one, two, three, four or more times.

8. The method of claim 1, wherein the fractionating step comprises centrifugation or differential filtration.

9. The method of claim 1, wherein the fractionating step utilizes targeted probes that specifically bind eukaryotic nucleic acid.

10. The method of claim 1, wherein i) step d) is repeated two or more times, ii) step e) is repeated two or more times, or iii) both step d) and step e) are repeated two or more times.

11. The method of claim 1, further comprising extracting the eukaryotic nucleic acids from the collected layer comprising eukaryotic nucleic acids.

12. The method of claim 1, wherein the extraction method is a magnetic particle-based, column-based, filter-based, bead-based, or organic solvent-based method.

13. The method of claim 1, wherein the nucleic acid comprises DNA, RNA, total RNA, mRNA, tRNA, rRNA, ncRNA, smRNA, or snoRNA, or a combination of any of DNA, RNA, total RNA, mRNA, tRNA, rRNA, ncRNA, smRNA, or snoRNA.

14. The method of claim 1, wherein the separating step comprises centrifugation.

15. The method of claim 1, wherein the extraction method comprises a magnetic particle-based method.

16. The method of claim 1, wherein the nucleic acid comprises RNA.

17. The method of claim 1, wherein the nucleic acid comprises mRNA.

18. The method of claim 1, further comprising a step of analyzing the extracted nucleic acid via microarray sequencing, molecular barcoding, probe capture, polymerase chain reaction (PCR), ddPCR, RT-PCR, RT-qPCR, or nucleic acid sequencing.

19. The method of claim 1, further comprising a step of analyzing the extracted nucleic acid via ddPCR.

20. The method of claim 1, further comprising a step of analyzing the extracted nucleic acid via PCR.

* * * * *

SEQUENCE LISTING

```
<160> NUMBER OF SEQ ID NOS: 32

<210> SEQ ID NO 1
<211> LENGTH: 18
<212> TYPE: DNA
<213> ORGANISM: Artificial Sequence
<220> FEATURE:
<223> OTHER INFORMATION: PCR primer

<400> SEQUENCE: 1
agaccgcgtc cacccgc                                                     18

<210> SEQ ID NO 2
<211> LENGTH: 20
```

```
<212> TYPE: DNA
<213> ORGANISM: Artificial Sequence
<220> FEATURE:
<223> OTHER INFORMATION: PCR primer

<400> SEQUENCE: 2
cgaagccggc cttgcacatg                                              20

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
atggtgaagg tcggagtcaa c                                            21

<210> SEQ ID NO 4
<211> LENGTH: 23
<212> TYPE: DNA
<213> ORGANISM: Artificial Sequence
<220> FEATURE:
<223> OTHER INFORMATION: PCR primer

<400> SEQUENCE: 4
gtgggtagaa tcatactgga aca                                          23

<210> SEQ ID NO 5
<211> LENGTH: 22
<212> TYPE: DNA
<213> ORGANISM: Artificial Sequence
<220> FEATURE:
<223> OTHER INFORMATION: PCR primer

<400> SEQUENCE: 5
agtgacctag cgtgtcattc tg                                           22

<210> SEQ ID NO 6
<211> LENGTH: 21
<212> TYPE: DNA
<213> ORGANISM: Artificial Sequence
<220> FEATURE:
<223> OTHER INFORMATION: PCR primer

<400> SEQUENCE: 6
gctgtctgga cccctta cat g                                           21

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7 ttcccccctca tcacctgtga                                             20

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
```

```
ggttgttgat tgcactgagg                                              20

<210> SEQ ID NO 9
<211> LENGTH: 21
<212> TYPE: DNA
<213> ORGANISM: Artificial Sequence
<220> FEATURE:
<223> OTHER INFORMATION: PCR primer

<400> SEQUENCE: 9
cagcctgaga gccgaggaca c                                            21

<210> SEQ ID NO 10
<211> LENGTH: 21
<212> TYPE: DNA
<213> ORGANISM: Artificial Sequence
<220> FEATURE:
<223> OTHER INFORMATION: PCR primer

<400> SEQUENCE: 10
tgaggagacg gtgaccaggg t                                            21

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
ggaggacaca aagagtgagg                                              20

<210> SEQ ID NO 12
<211> LENGTH: 20
<212> TYPE: DNA
<213> ORGANISM: Artificial Sequence
<220> FEATURE:
<223> OTHER INFORMATION: PCR primer

<400> SEQUENCE: 12
accctgagaa ttgtgccagg                                              20

<210> SEQ ID NO 13
<211> LENGTH: 20
<212> TYPE: DNA
<213> ORGANISM: Artificial Sequence
<220> FEATURE:
<223> OTHER INFORMATION: PCR primer

<400> SEQUENCE: 13
gttactataa acctggtaac                                              20

<210> SEQ ID NO 14
<211> LENGTH: 27
<212> TYPE: DNA
<213> ORGANISM: Artificial Sequence
<220> FEATURE:
<223> OTHER INFORMATION: PCR primer

<400> SEQUENCE: 14
tctgggrtgt aytactgtgc tgtctgg                                      27

<210> SEQ ID NO 15
<211> LENGTH: 20
<212> TYPE: DNA
<213> ORGANISM: Artificial Sequence
```

```
<220> FEATURE:
<223> OTHER INFORMATION: PCR primer

<400> SEQUENCE: 15
gccaaccgtg agaagatgac                                              20

<210> SEQ ID NO 16
<211> LENGTH: 20
<212> TYPE: DNA
<213> ORGANISM: Artificial Sequence
<220> FEATURE:
<223> OTHER INFORMATION: PCR primer

<400> SEQUENCE: 16
ggagaagaac agaaccctgg                                              20

<210> SEQ ID NO 17
<211> LENGTH: 22
<212> TYPE: DNA
<213> ORGANISM: Artificial Sequence
<220> FEATURE:
<223> OTHER INFORMATION: PCR primer

<400> SEQUENCE: 17
cggatttggc cgtattgggc gc                                           22

<210> SEQ ID NO 18
<211> LENGTH: 29
<212> TYPE: DNA
<213> ORGANISM: Artificial Sequence
<220> FEATURE:
<223> OTHER INFORMATION: PCR primer

<400> SEQUENCE: 18
ggtggaatca tactggaaca tgtagacca                                    29

<210> SEQ ID NO 19
<211> LENGTH: 23
<212> TYPE: DNA
<213> ORGANISM: Artificial Sequence
<220> FEATURE:
<223> OTHER INFORMATION: PCR primer

<400> SEQUENCE: 19
ggsagaagag cgacgagggc gtg                                          23

<210> SEQ ID NO 20
<211> LENGTH: 23
<212> TYPE: DNA
<213> ORGANISM: Artificial Sequence
<220> FEATURE:
<223> OTHER INFORMATION: PCR primer

<400> SEQUENCE: 20
gggcgaagag cgatgaggga gtg                                          23

<210> SEQ ID NO 21
<211> LENGTH: 23
<212> TYPE: DNA
<213> ORGANISM: Artificial Sequence
<220> FEATURE:
<223> OTHER INFORMATION: PCR primer

<400> SEQUENCE: 21
gtagtgagga gratgctggt ctg                                          23
```

<210> SEQ ID NO 22
<211> LENGTH: 23
<212> TYPE: DNA
<213> ORGANISM: Artificial Sequence
<220> FEATURE:
<223> OTHER INFORMATION: PCR primer

<400> SEQUENCE: 22
ggcagaagca tgacaagggc atg                                              23

<210> SEQ ID NO 23
<211> LENGTH: 22
<212> TYPE: DNA
<213> ORGANISM: Artificial Sequence
<220> FEATURE:
<223> OTHER INFORMATION: PCR primer

<400> SEQUENCE: 23
agktttmytt cagcaattgm gg                                               22

<210> SEQ ID NO 24
<211> LENGTH: 21
<212> TYPE: DNA
<213> ORGANISM: Artificial Sequence
<220> FEATURE:
<223> OTHER INFORMATION: PCR primer

<400> SEQUENCE: 24
ccctgagcag tgtgccagsa c                                                21

<210> SEQ ID NO 25
<211> LENGTH: 26
<212> TYPE: DNA
<213> ORGANISM: Artificial Sequence
<220> FEATURE:
<223> OTHER INFORMATION: PCR primer

<400> SEQUENCE: 25
gggggagtta ckatgasctt arttcc                                           26

<210> SEQ ID NO 26
<211> LENGTH: 26
<212> TYPE: DNA
<213> ORGANISM: Artificial Sequence
<220> FEATURE:
<223> OTHER INFORMATION: PCR primer

<400> SEQUENCE: 26
atccagatct caggtttggg aggagg                                           26

<210> SEQ ID NO 27
<211> LENGTH: 17
<212> TYPE: DNA
<213> ORGANISM: Artificial Sequence
<220> FEATURE:
<223> OTHER INFORMATION: PCR primer

<400> SEQUENCE: 27
ccaggctcca gggmggg                                                     17

<210> SEQ ID NO 28
<211> LENGTH: 21
<212> TYPE: DNA
<213> ORGANISM: Artificial Sequence
<220> FEATURE:
<223> OTHER INFORMATION: PCR primer

```
<400> SEQUENCE: 28
tccagagaca acgccaagaa c                                         21

<210> SEQ ID NO 29
<211> LENGTH: 21
<212> TYPE: DNA
<213> ORGANISM: Artificial Sequence
<220> FEATURE:
<223> OTHER INFORMATION: PCR primer

<400> SEQUENCE: 29
gttcggrcgr ctrctsgttt c                                         21

<210> SEQ ID NO 30
<211> LENGTH: 19
<212> TYPE: DNA
<213> ORGANISM: Artificial Sequence
<220> FEATURE:
<223> OTHER INFORMATION: PCR primer

<400> SEQUENCE: 30
acaccgtcac cagggctcc                                            19

<210> SEQ ID NO 31
<211> LENGTH: 24
<212> TYPE: DNA
<213> ORGANISM: Artificial Sequence
<220> FEATURE:
<223> OTHER INFORMATION: PCR primer

<400> SEQUENCE: 31
tgaggacact gtgactatgg ttcc                                      24

<210> SEQ ID NO 32
<211> LENGTH: 21
<212> TYPE: DNA
<213> ORGANISM: Artificial Sequence
<220> FEATURE:
<223> OTHER INFORMATION: PCR primer

<400> SEQUENCE: 32
ggacaccgtc acyakgvytc c                                         21
```